US007894646B2

(12) United States Patent
Shirahata et al.

(10) Patent No.: US 7,894,646 B2
(45) Date of Patent: Feb. 22, 2011

(54) MEDICAL IMAGE DIAGNOSIS SUPPORT DEVICE AND METHOD FOR CALCULATING DEGREE OF DEFORMATION FROM NORMAL SHAPES OF ORGAN REGIONS

(75) Inventors: Takashi Shirahata, Chiba (JP); Yoshihiro Goto, Tokyo (JP); Toru Nakagawa, Ibaraki (JP)

(73) Assignee: Hitachi Medical Corporation, Tokyo (JP)

( * ) Notice: Subject to any disclaimer, the term of this patent is extended or adjusted under 35 U.S.C. 154(b) by 797 days.

(21) Appl. No.: 10/566,666

(22) PCT Filed: Jul. 29, 2004

(86) PCT No.: PCT/JP2004/010835
§ 371 (c)(1),
(2), (4) Date: Jan. 27, 2006

(87) PCT Pub. No.: WO2005/011501

PCT Pub. Date: Feb. 10, 2005

(65) Prior Publication Data
US 2006/0280347 A1 Dec. 14, 2006

(30) Foreign Application Priority Data

| Aug. 1, 2003 | (JP) | ............................. 2003-284919 |
| Sep. 5, 2003 | (JP) | ............................. 2003-313424 |
| Apr. 13, 2004 | (JP) | ............................. 2004-117734 |

(51) Int. Cl.
*G06K 9/00* (2006.01)
*G06K 9/46* (2006.01)
*G06K 9/48* (2006.01)
*G06K 9/66* (2006.01)

(52) U.S. Cl. ....................... 382/128; 382/190; 382/195; 382/199

(58) Field of Classification Search .................. 382/128, 382/130–132, 100, 103, 108, 141, 144, 145, 382/147, 149, 152, 154–156, 170, 165, 190, 382/195, 197, 199, 203–231
See application file for complete search history.

(56) References Cited

U.S. PATENT DOCUMENTS 6,167,167 A * 12/2000 Matsugu et al. ............. 382/283

(Continued)

FOREIGN PATENT DOCUMENTS

JP 8-336524 12/1996

(Continued)

OTHER PUBLICATIONS

Yoshitaka, et al., Region-Growing based feature extraction algorithm for tree-like objects, Visualization in Biomedical Computing, Springer Berlin/Heidelberg, vol. 1131/1996, copyright 1996, pp. 159-171.*

(Continued)

*Primary Examiner*—Tom Y Lu
*Assistant Examiner*—Thomas A Conway
(74) *Attorney, Agent, or Firm*—Cooper & Dunham LLP

(57) ABSTRACT

A medical image diagnosis support device comprises an organ region setting means, a deformation degree calculating means for calculating the deformation degree of the organ region set by the organ region setting means, a reference value storing means, a lesion detecting means for comparing the stored reference value with the deformation degree calculated by the deformation calculating means and for detecting existence of a lesion of the organ region from the comparison result, and a presenting means for presenting the existence to the examiner at least either visually or auditorily. Thus, the device can make a diagnosis selectively only on an organ region deformed because of a lesion and present it to the examiner visually such as by means of an image display or auditorily such as by means of speech, thereby improving the efficiency of diagnosis.

20 Claims, 32 Drawing Sheets

U.S. PATENT DOCUMENTS

| | | | | |
|---|---|---|---|---|
| 6,301,498 | B1 * | 10/2001 | Greenberg et al. | 600/425 |
| 6,643,533 | B2 * | 11/2003 | Knoplioch et al. | 600/407 |
| 7,616,789 | B2 * | 11/2009 | Oosawa | 382/128 |
| 2001/0039421 | A1 * | 11/2001 | Heilbrun et al. | 606/130 |
| 2001/0043729 | A1 * | 11/2001 | Giger et al. | 382/128 |
| 2002/0076108 | A1 * | 6/2002 | Konoshima et al. | 382/217 |

FOREIGN PATENT DOCUMENTS

| | | | |
|---|---|---|---|
| JP | 2002-207992 | | 7/2002 |
| JP | 2002207992 A | * | 7/2002 |
| JP | 2003-70781 | | 3/2003 |

OTHER PUBLICATIONS

Swett et al. (Expert system-controlled image display, Aug. 1989 Radiology, 172, pp. 487-493).*

Huo et al. (Analysis of spiculation in the computerized classification of mammographic masses, Med. Phys., vol. 22, Issue 10, pp. 1569-1579).*

Declerck et al. (Automatic registration and alignment on a template of cardiac stress and rest SPECT images, Mathematical Methods in Biomedical Image Analysis Proceedings on, 1996, pp. 212-221).*

* cited by examiner

FIG. 38
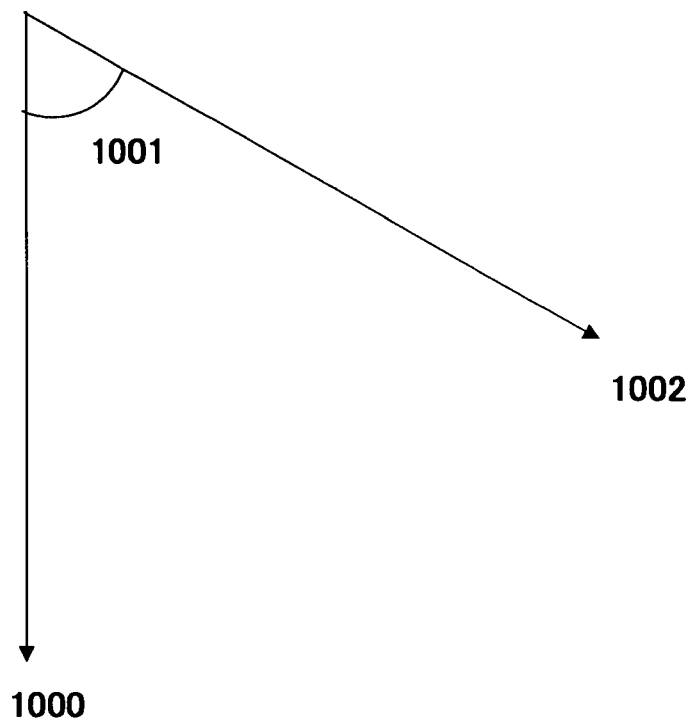
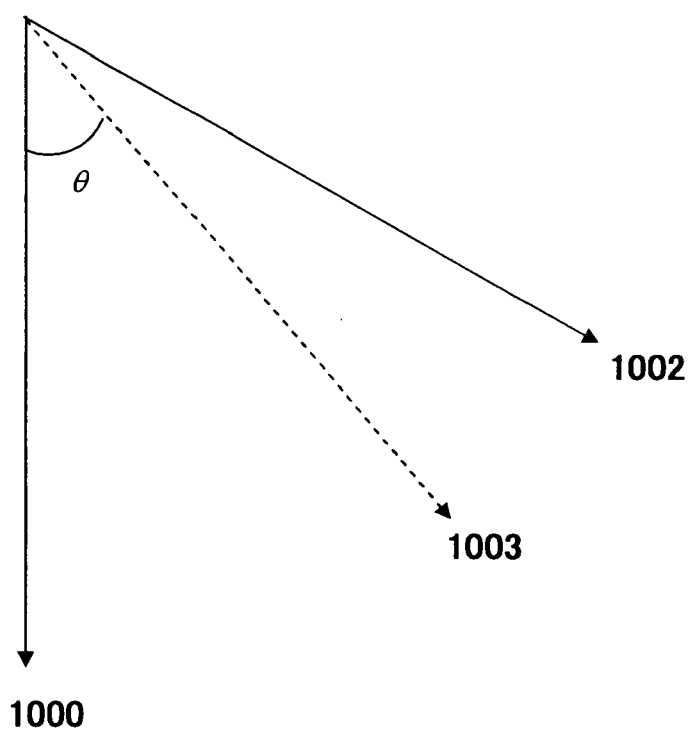

MEDICAL IMAGE DIAGNOSIS SUPPORT DEVICE AND METHOD FOR CALCULATING DEGREE OF DEFORMATION FROM NORMAL SHAPES OF ORGAN REGIONS

TECHNICAL FIELD

The present invention relates to a medical image diagnosis support device for supporting image diagnosis using a medical image obtained from a medical image diagnostic apparatus (including MRI apparatus, X-ray CT apparatus, and ultrasonic diagnostic apparatus), and in particular to a medical image diagnosis support device for supporting a diagnosis for organ regions with different figurations according to the symptom of a subject.

BACKGROUND OF THE INVENTION

The examination of a tumor for a subject has been executed by obtaining images with endoscopes being intubated into the hollow viscera regions such as trachea, respiratory system, and intestinal canal.

However, the above examinations have been imposing a strain on the subjects such as the pain of intubating the endoscopes into the hollow viscera regions of the subjects.

Virtual endoscopy described in Patent Document 1 cut down the burden on the subject because it uses data of X-ray CT images that provides images that are equivalent to those of endoscopes and thus intubation of the endoscopes is unnecessary.

However, virtual endoscopy described in the Patent Document 1 has the disadvantage of having a narrow view for display, thus it takes a long time to perform an examination on each patient since the whole hollow viscera region such as a trachea has to be diagnosed with a narrow field of view. The demand for improving the efficiency of diagnosis is not mentioned in the document.

Patent Document 1: JP-A-2002-238887

SUMMARY

In an aspect of this disclosure, there is provided a medical image diagnosis support device that comprises:

an organ region setting means for setting the organ region from the medical image of the subject obtained by a medical imaging device;

a deformation degree calculating means for calculating the deformation degree of the organ region set by the organ region setting means;

a reference value storing means for storing the index of the deformation degree of the organ region as a reference value;

a lesion detecting means for comparing the reference value stored in the reference value storing means with the deformation degree calculated by the deformation degree calculating means and for detecting existence of a lesion of the organ region from the comparison result; and a presenting means that presents the existence of a lesion to the examiner visually and/or auditorily.

The above-mentioned device enables selective diagnosis on just the distorted area of an organ and presentation of deformation in the diagnostic region visually and auditorily using such as images and voices, which lead to improved diagnosis efficiency.

According to one preferred embodiment of the present invention, the reference value storing means stores a plurality of templates according to the deformation degree of the organ region.

This helps to specify the object of comparison from a plurality of templates, and makes it easier for the examiner to grasp the stage of lesion progression.

According to one preferred embodiment of the present invention, the deformation degree calculating means comprises:

a cross-sectional image calculating means for calculating the cross-sectional images orthogonal toward the body axis direction of the organ region; and an extracting means for extracting the lumen and the external portion of the organ region from the cross-sectional images being calculated by the cross-sectional image calculating means, and calculates the deformation degree of the lumen and external portion of the organ region being extracted by the extracting means.

This enables to detect the protruding lesion such as a tumor or a stenosis that arise in the lumen of the organ region.

According to one preferred embodiment of the present invention, the presenting means presents the existence of a lesion being identified by the lesion detecting means and displays it visually in color for the examiner. To give a concrete example, the visualization is executed by displaying cross-sectional images of the organ region being set by the organ region setting means, and by highlighting the lesion candidate portions being detected by the lesion detecting means on the cross-sectional images.

This makes it possible for the examiner to visually identify the existence of a lesion by colors and other visual aids, and enhances the ease in detection of a lesion.

According to one preferred embodiment of the present invention, the presentation means presents the information to the hearing of the examiner, by outputting the condition being detected by the lesion detecting means auditorily.

This also helps easy detection of a lesion since the examiner is able to identify the condition of the detected information auditorily through sounds and voice messages.

According to one preferred embodiment of the present invention, a medical image diagnosis support device further comprises:

a cross-sectional image extracting means for extracting the cross-sections from the feature quantity of a hollow viscera in tomographic images being obtained from a medical imaging device;

a physical quantity calculating means for performing an arithmetic operation on the physical quantity including radius, degree of circularity and the gravity point of a hollow viscera on the cross section of a hollow viscera extracted by the extracting means;

a region of interest calculation means for calculating the region of interest based on the physical quantity being calculated by the physical quantity calculating means;

a 3-dimentional image creating means for creating a 3-dimentional image of the hollow viscera from a tomographic image including cross-sectional images of the hollow viscera being extracted by the cross-sectional image extracting means in the region of interest being calculated by the region of interest calculation means; and an image display means for displaying 3-dimentional images being created by the 3-dimentional image creating means.

Thus, a proper extraction of the organ region can be executed by the set threshold, which leads to a more precise configuration of 3-dimensional images.

According to one preferred embodiment of the present invention, a center-line calculating means for calculating the center line of hollow viscera based on the gravity point of the cross-section of the hollow viscera being calculated by the physical quantity calculating means is further comprised, and the center line being calculated by the center line calculation means and the 3-dimentional images being created by the 3-dimentional image creating means are displayed together on the image display means.

In another aspect of this disclosure, there is provided a medical image diagnosis support method that comprises:

an organ region setting step for setting the organ region from the medical images of a subject being obtained by a medical imaging device;

a deformation degree calculating step for calculating the deformation degree of the organ region being set by the organ region setting step;

a reference value storing step for storing the deformation degree index of the organ region as a reference value;

a lesion detecting step for comparing the reference value being stored by the reference value storing step and the deformation degree being calculated by the deformation degree calculating step, and detecting the existence of the lesion in the organ region from the result of the comparison; and a presenting step for presenting the existence of the lesion in the organ region being detected by the lesion detecting step visually and/or auditorily.

Such steps result in improving the efficiency of diagnosis, by enabling selective diagnose of only the deformed portion in the organ region, and by presenting the deformation of the diagnosed region to the examiner visually and/or auditorily through means such as image displays and voice messages.

BRIEF DESCRIPTION OF THE DRAWINGS

FIG. 38 is a diagram explaining a setting method of the variable ROI-setting threshold value.

BEST MODE FOR IMPLEMENTING THE INVENTION

Hereinafter, preferred embodiments of an X-ray image diagnosis support device relating to the present invention will be described with reference to the drawings.

Figure 1:
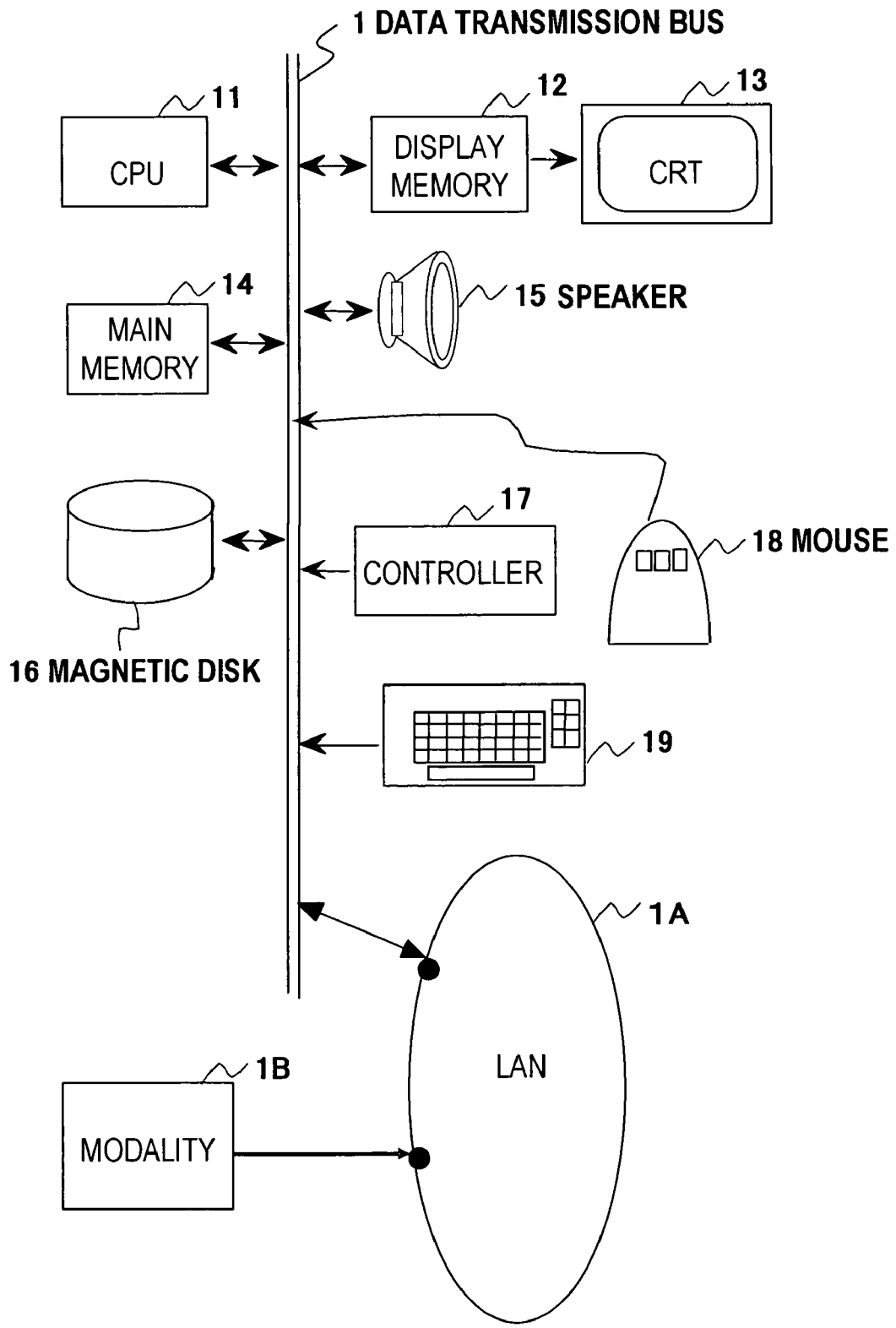
FIG. 1 is a block diagram illustrating an example of a medical image display device that is common to the respective embodiments of the present invention.

FIG. 1 is a block diagram illustrating an example of the medical image display device that is common to the respective embodiments of the present invention.

A medical image display device, as illustrated in FIG. 1, includes display memory 12, CRT 13, main memory 14, speaker 15, magnetic disk 16, controller 17, mouse 18, keyboard 19, local area network (LAN) 1A that are respectively and electrically connected to CPU 11 via transmission bus 1C, and modality 1B being electrically connected to LAN1A.

CPU 11 performs the overall control of display memory 12, CRT 13, main memory 14, speaker 15, magnetic disk 16, controller 17, mouse 18, and keyboard 19 that are constituent being electrically connected to data transmission bus 1C, and also controls the transmission to LAN 1A and the reception from LAN 1A.

Display memory 12 temporarily stores the image data being display outputted to CRT 13.

CRT 13 is a display device for reading out the image data being stored in display memory 12 and for displaying those image data. Though this device exemplifies CRT, various types of display such as plasma and liquid crystal are included in the display device being described here.

Main memory 14 stores data for processing in CPU 11 and the programs for executing in CPU 11.

Speaker 15, though not shown in the diagram, includes a storage unit for storing the voice data for phonetic output, and can generate the voice by reading out the voice data being stored in the storage unit.

Magnetic disk 16, as same as main memory 14, stores data for processing in CPU 11 and the programs for executing in CPU 11, and is an external device which has more storage capacity than main memory 14. External devices, other than the magnetic disk, media such as CD, MD and DVD and RAM disk can be substituted or shared.

Controller 17 carries out the function to measure the form of the organ region and to detect the existence of lesion from the measured form of the organ region. The details will be explained later with reference to FIG. 2.

Mouse 18 is for the examiner to designate the discretional regions of images being displayed on CRT 12, or to selectively input the buttons being displayed on the screen of CRT 11.

Keyboard 19 has the same function as mouse 18, and also for inputting the character information such as ID of the patients.

LAN 1A is, for example, the network equipment being installed in the hospitals. This network equipment can be a wide-area network through an exclusive line or Internet.

Modality 1B is a medical image diagnostic device such as an X-ray device, X-ray CT device, MRI device, or ultrasound device. Here an X-ray CT device will be exemplified.

For data transmission bus 1C, other than the standardized PCI (Peripheral Component Interconnect) bus and the like, the data transmission buses that are compliant with the standard such as USB (Universal Serial Bus) and IEEE 1394 can be adopted.

Next, a configuration example of controller 17 will be described referring to FIG. 2.

Figure 2:
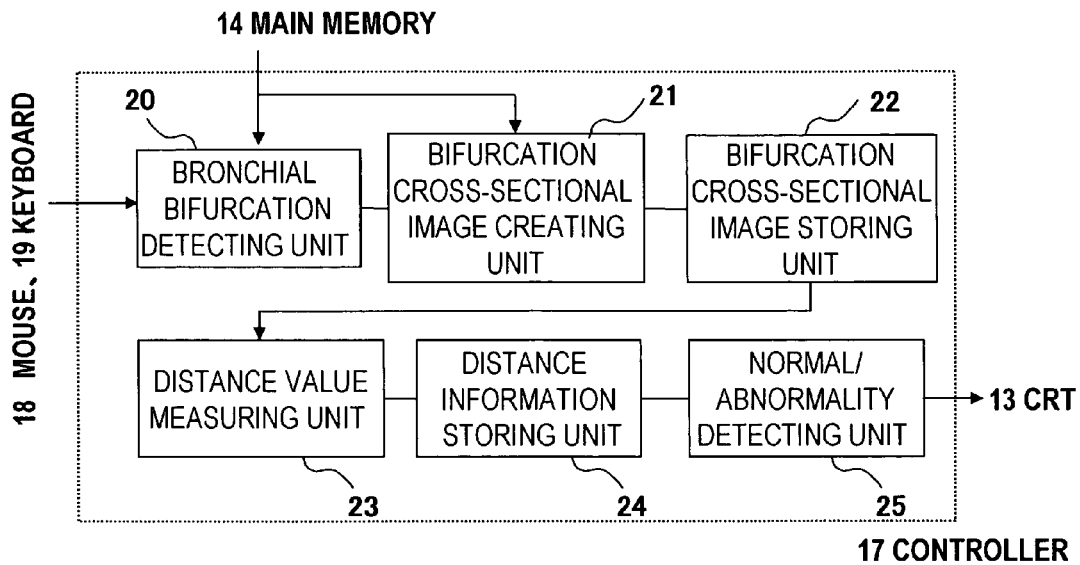
FIG. 2 is a block diagram illustrating the detailed example of a controller in FIG. 1 for explaining the first and the second embodiments.

FIG. 2 is a block diagram illustrating a detailed example of a controller in FIG. 1 for explaining the first and the second embodiments. Here a hollow viscera region is bronchi.

Controller 17, as illustrated in FIG. 2, includes:
bronchi bifurcation detecting unit 20 being electrically connected to mouse 18, keyboard 19 and main memory 14;
bifurcation cross-sectional image creating unit 21 being electrically connected to bronchi bifurcation detecting unit 20 and main memory 14;
bifurcation cross-sectional image storing unit 22 being electrically connected to bifurcation cross-sectional image creating unit 21;
distance measuring unit 23 being electrically connected to bifurcation cross-sectional image storing unit 22;
distance information storing unit 24 being electrically connected to distance measuring unit 23; and
normal/abnormality detecting unit 25 being electrically connected to distance information storing unit 24.

Bronchi bifurcation detecting unit 20 detects the bifurcation of bronchi using the medical images being inputted from modality 18 or the bronchi detection images in which the bronchi region is detected from the medical images, or medical images and/or detection images being stored in the external storage device such as main memory 14 and magnet disk 16. The detection can be performed either manually by an operator using the input device such as mouse 18, or by using the bifurcation coordinate being obtained in advance and stored in main memory 14 or the external device.

Bifurcation cross-sectional image creating unit 21 creates the cross-sectional images of the bronchi bifurcation from the medical images or the bronchi region detecting images being stored in main memory 14.

Bifurcation cross-sectional image storing unit 22 stores the bronchi bifurcation cross-sectional images being created by bifurcation cross-sectional image creating unit 21.

Distance measuring unit 23 measures the distance between the parts of bronchi after bifurcation using the bronchi bifurcation cross-sectional images being stored in the bifurcation sectional image storing unit.

Distance information storing unit 24 stores the distance information between the 2 parts of bronchi after bifurcation, being measured by distance measuring unit 23.

Normal/abnormality detecting unit 25 detects whether the form of the bifurcation is normal or abnormal based on the distance information between the 2 parts of bronchi after bifurcation, being measured by distance measuring unit 23 referring to the reference value (templates), and displays whether normal or abnormal based on the detecting result of the bifurcation forms. Templates here are the plurality of the following templates being stored as a reference:
a normal case template created from the distance information based on the normal case without lesion;
a moderate case template created from the distance information based on the case in which a moderate lesion is recognized;
a medium case template created from the distance information based on the case in which a medium-degree of lesion is recognized;
a serious case template created from the distance information based on the case in which a serious lesion is recognized. The closest to the respective templates will be the detection result, but the ones between the templates will be obtained by interpolating the data of the respective normal, moderate, medium and serious templates. For example, if one cased in recognized between a moderate and medium-degree case, it will be recognized as a moderate/medium case.

Next, the operation of the respective embodiments will be described referring to the drawings.

The First Embodiment

Figure 3:
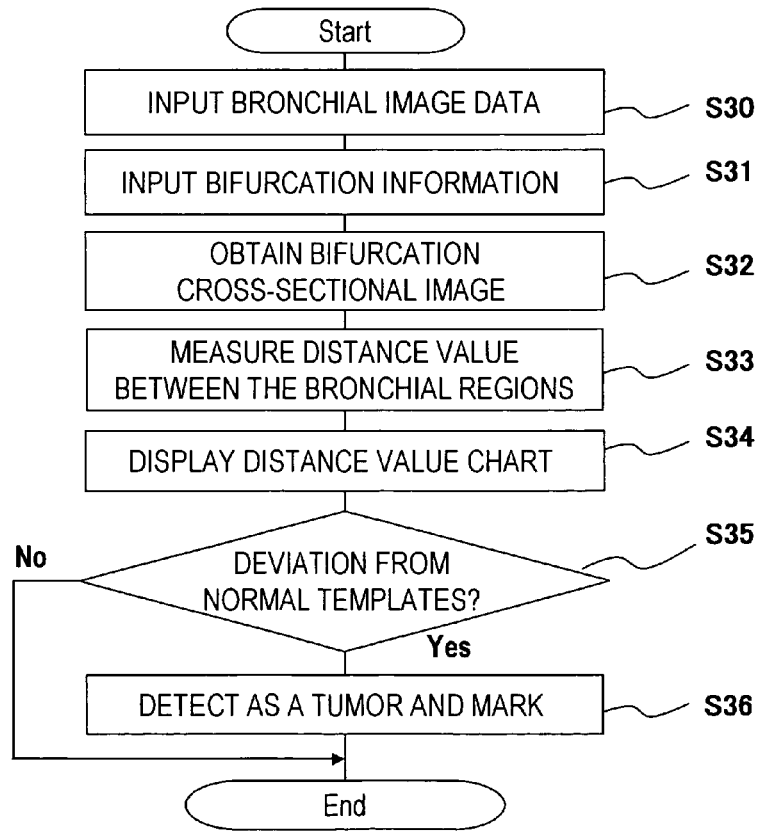
FIG. 3 is a flow chart for explaining the operation example of the first embodiment.

FIG. 3 is a flow chart explaining the operation example of the first embodiment, and FIGS. 4 to 8 are the explanatory diagrams of steps S31~S36 in FIG. 3.

(Step S30)

An examiner (an operator) operates mouse 18 or other input device, and inputs to controller 17 the medical image data being read out from main memory 14.

(Step S31)

The examiner (the operator) operates mouse 18, and inputs to controller 17 the bronchi bifurcation information from main memory 14 or other memory device. The bifurcation information here indicates the coordinate of the bifurcation and the direction vector of the bifurcation. The direction vector of the bifurcation indicates the vector that points to the direction of the bronchi right before the bifurcation as arrow 41 in FIG. 4.

(Step S32)

Figure 4:
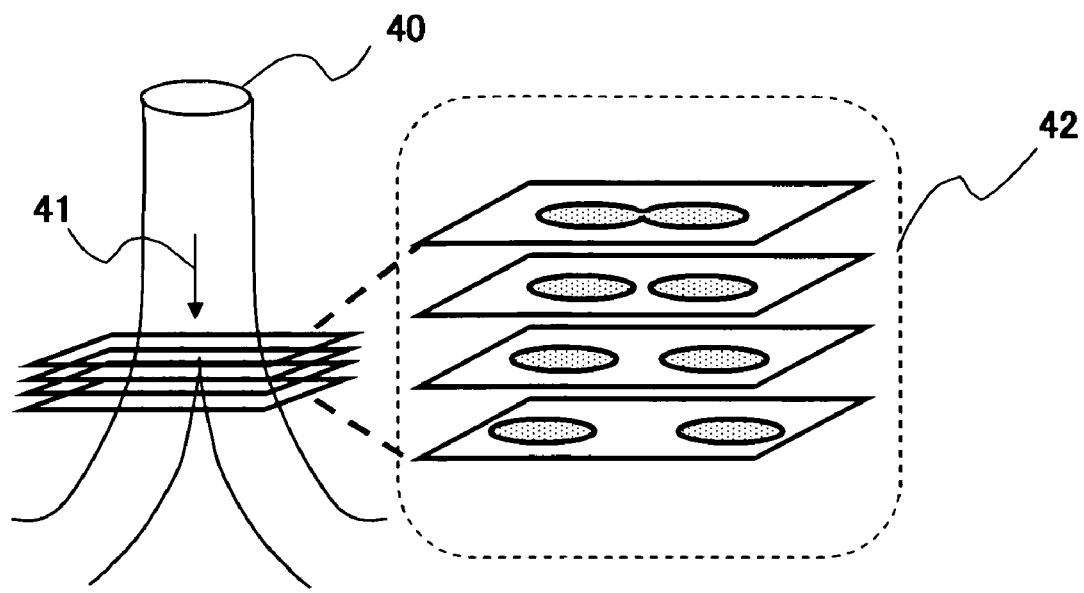
FIG. 4 is an explanatory diagram of step S32 in FIG. 3.

Controller 17 creates the several pieces of the cross-sectional images that are orthogonal to the direction vector of the bifurcation as seen in a group of cross-sectional images 42 in FIG. 4.

(Step S33)

Controller 17 calculates the distance between the bronchi regions in the created cross-sectional images.

Figure 5:
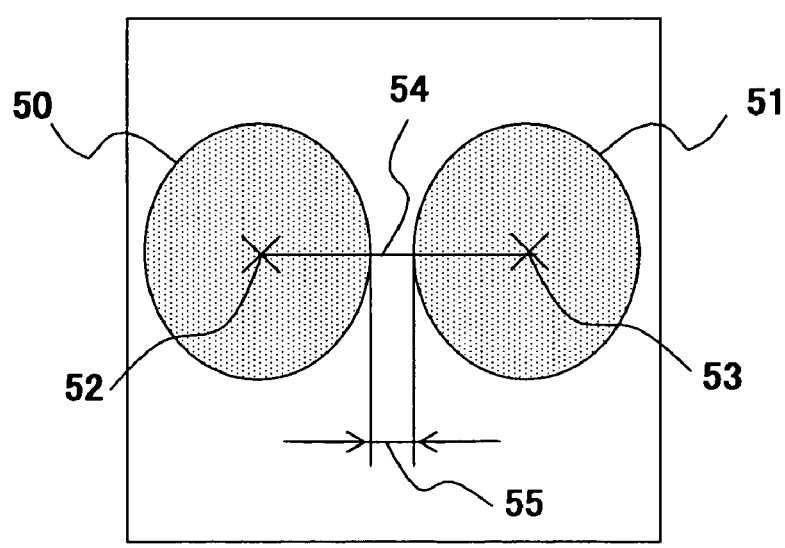
FIG. 5 is an explanatory diagram of step S33 in FIG. 3.

Here the distance can be either the minimum distance between the peripheries of the bronchi region or the bronchi spacing distance 55 on segment 54 that is connecting gravity points 52 and 53 of bronchi region 50 and 51 in FIG. 5.

(Step S34)

Figure 6:
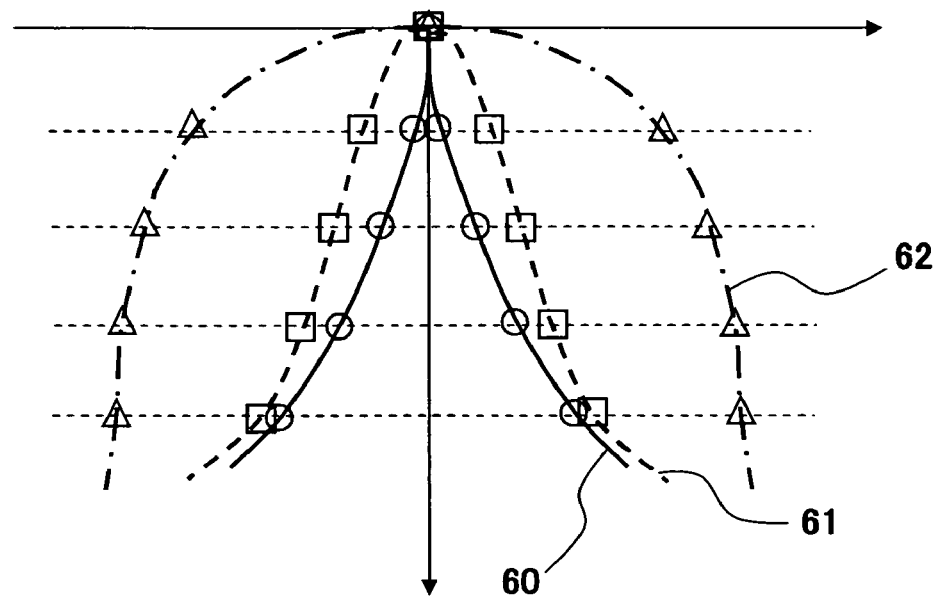
FIG. 6 is an explanatory diagram of step S34 in FIG. 3.

Controller 17 creates a chart corresponding to the cross-sectional image position of the spacing distance of bronchi as illustrated in FIG. 6 using the bronchi spacing distance data.

(Step S35)

Figure 7:
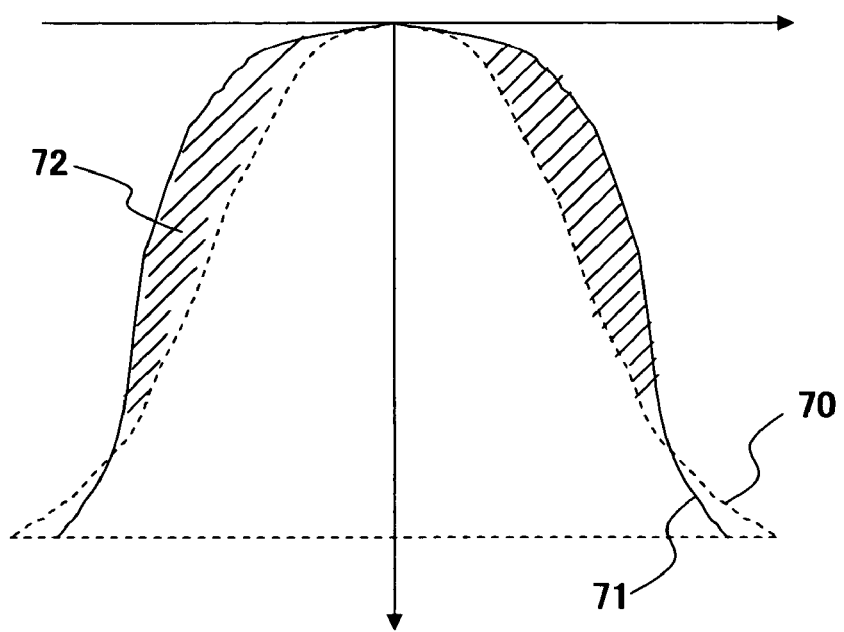
FIG. 7 is an explanatory diagram of step S35 in FIG. 3.

Controller 17 detects whether the form of the bronchi bifurcation is normal or abnormal based on the created chart. If normal, a sharp figure is formed as seen in curve 60 or curve 61 in FIG. 6. On the other hand, if a lesion such as a tumor exists, a broadened figure is formed as seen in curve 62. As seen in FIG. 7, by setting reference curve 70 (normal template), if curve 71 of the created chart is outside of the reference curve 70 it is judged as a lesion candidate, and if inside of the reference curve it is judged as normal. Practically area ratio r between the area being framed by curve 71 indicating the obtained bronchi spacing distance and area 72 being protruded to the outside of area 70 are calculated. Also, threshold T is set in advance for detecting normal/abnormality of this area ratio r. When the calculated area ratio r is more than threshold T it is determined that the form is abnormal, and when less than threshold it is determined as normal. The reference curve and the threshold here are the quantity being obtained by a large number of clinical data and statistically calculated. Threshold T can be set as its option by the input devices of mouse 18 or keyboard 19.

(Step S36)

Figure 8:
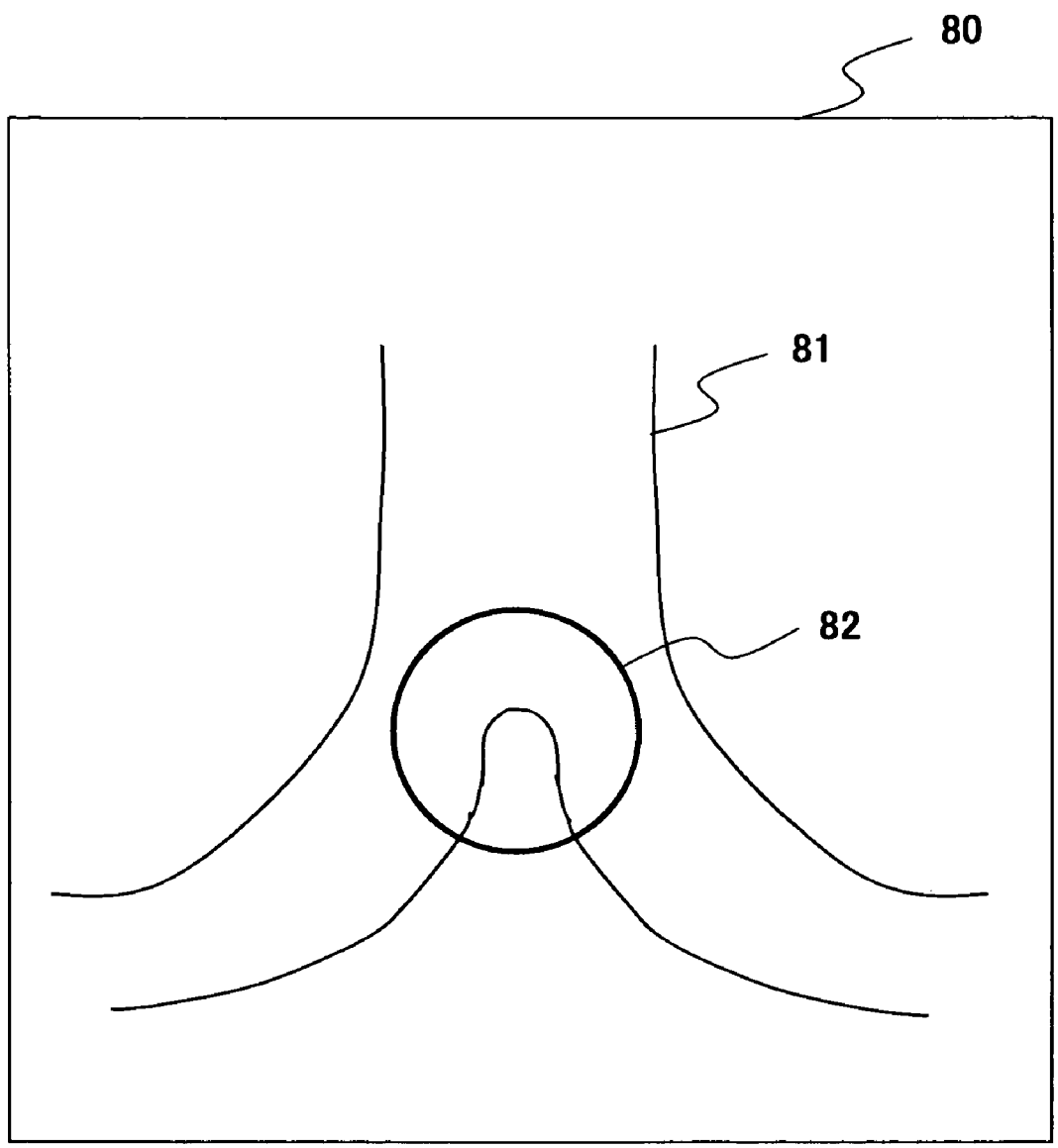
FIG. 8 is an explanatory diagram of step S36 in FIG. 3.

Controller 17, when the bifurcation is determined as deformed by a lesion, as illustrated in notable cross-sectional image 80 in FIG. 8, draws the attention of the examiner by surrounding the bifurcation of bronchi 81 with a circle 82 and highlighting it. Also, for the style of highlighting, color tinting only the bifurcation can be used for display instead of using circle 82.

Also, for example, when the lumen of bronchi is being viewed as aided by virtual endoscopy, the bifurcation with a lesion candidate can be displayed with different colors in advance. Instead of changing the colors, it can be set so that the notification will be made to the examiner with voice and/or sound when virtual endoscopy passes through the vicinity of the bifurcation. Needless to say the notification can be made using both colors and voice/sound.

According to the above-mentioned embodiments, a lesion candidate formed on the bifurcation of bronchi can be detected.

The burden of the doctor (examiner) will thus be lightened.

The Second Embodiment

Figure 9:
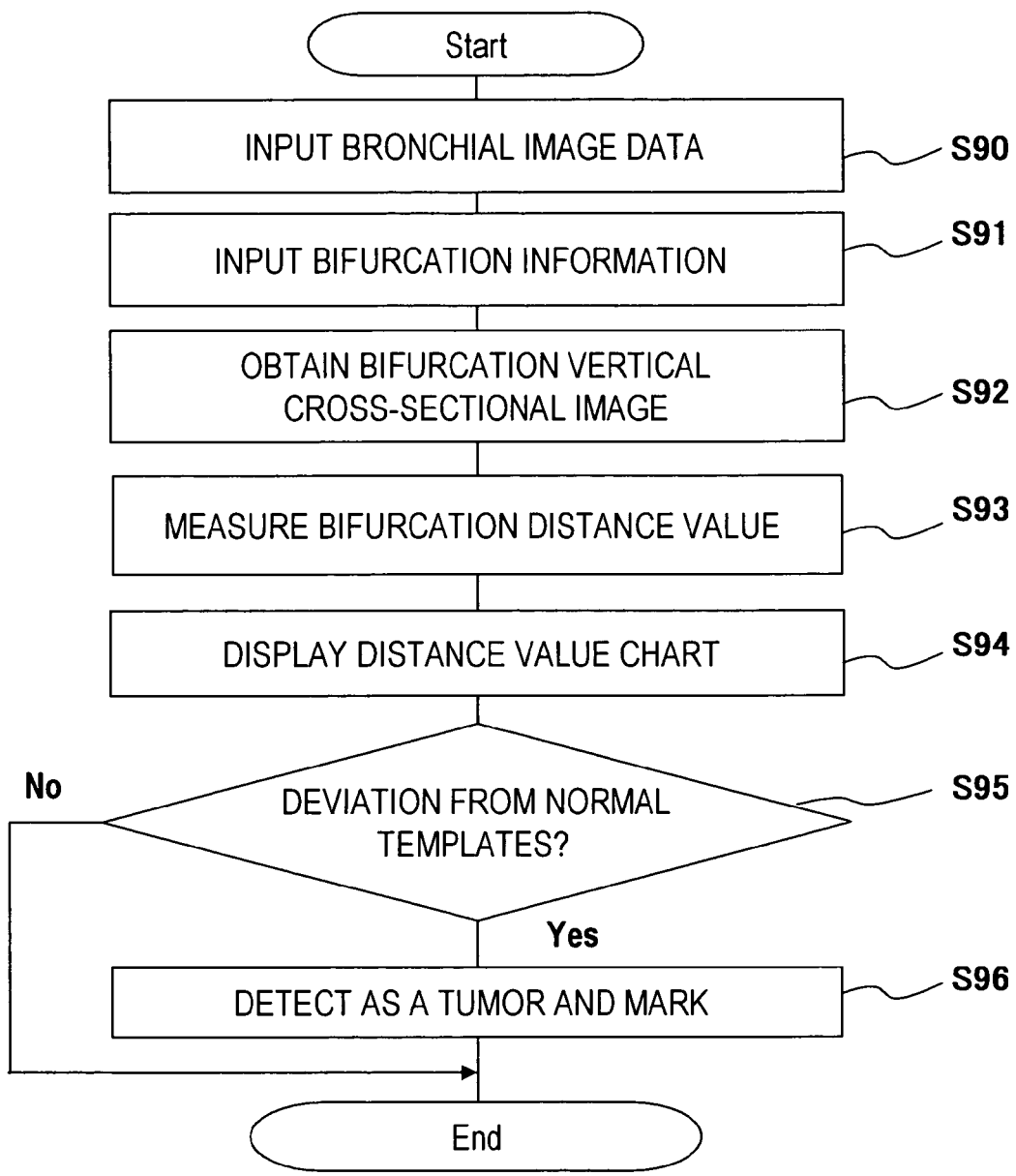
FIG. 9 is a flow chart explaining the operation example of the second embodiment.
Figure 10:
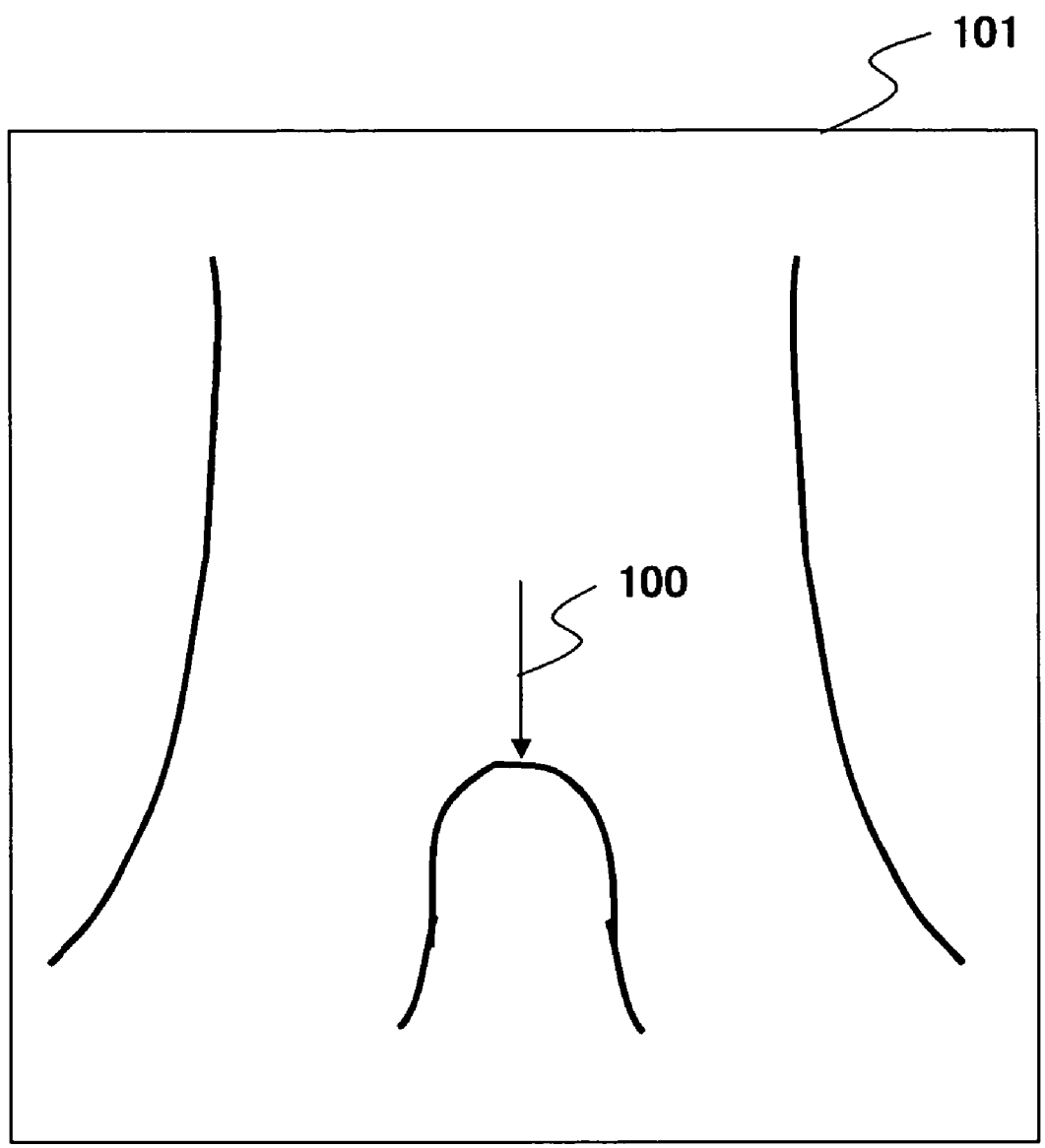
FIG. 10 is an explanatory diagram of step S92 in FIG. 9.
Figure 11:
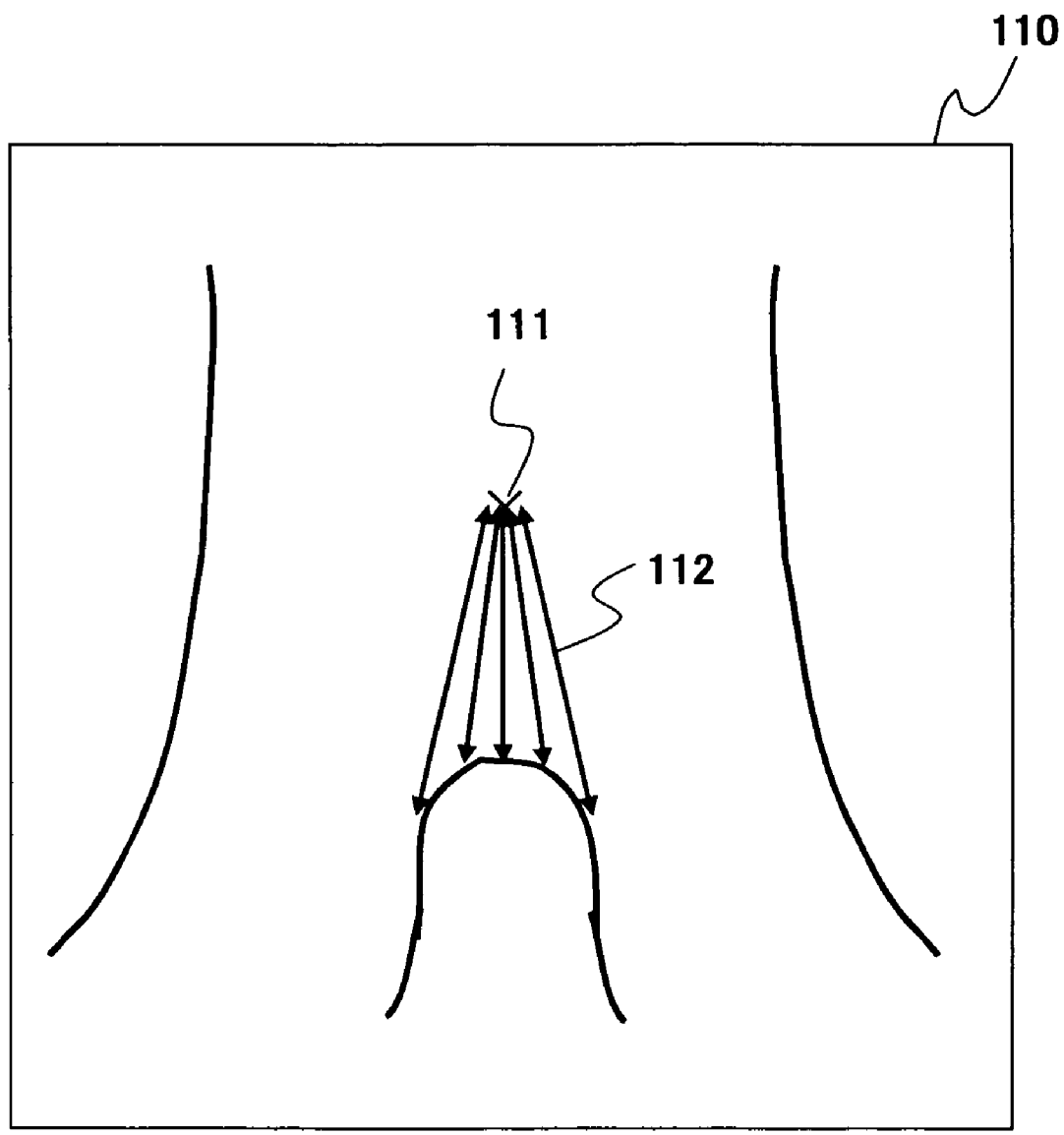
FIG. 11 is an explanatory diagram of step S93 in FIG. 9.
Figure 12:
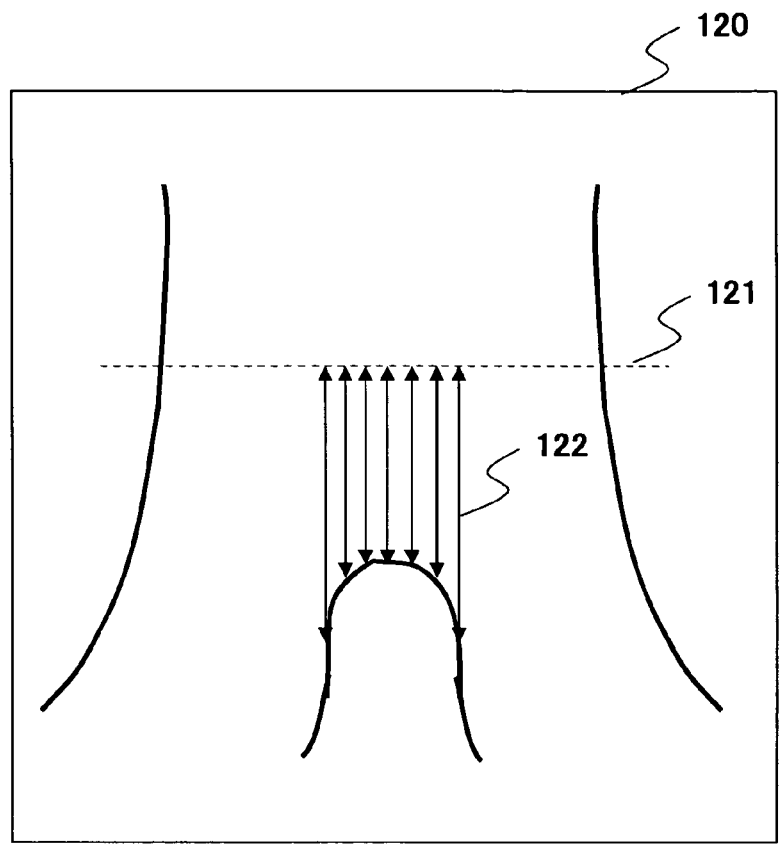
FIG. 12 is an explanatory diagram of step S93 differing from FIG. 11.
Figure 13:
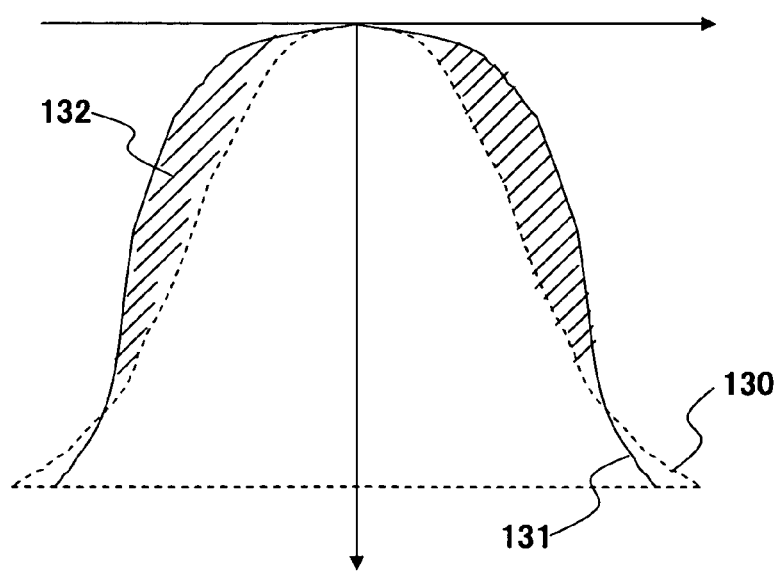
FIG. 13 is an explanatory diagram of step S95 in FIG. 9.

FIG. 9 is a flow chart explaining an operation example of the second embodiment, FIG. 10 is an explanatory diagram of step S92 in FIG. 9, FIGS. 11 and 12 are the explanatory diagrams of step S93 in FIG. 9, and FIG. 13 an explanatory diagram of step S95 in FIG. 9.

(Step S90)

An operator operates mouse 18 or other input device, and inputs the medical image data being read out from main memory 14 or other memory device to controller 17.

(Step S91)

The operator operates mouse 18, and inputs the information on bronchi bifurcation from main memory 14 to controller 17. The information on the bronchi bifurcation here means coordinates of the bifurcation and the vector direction of the bifurcation.

(Step S92)

Controller 17 creates cross-sectional image 101 including vector direction 100 of the bifurcation as seen in FIG. 10, based on the inputted medical image data and the information of the bronchi bifurcation.

(Step S93)

Controller 17 calculates distance 112 that is the distance from reference point 111 to the respective points of the bronchi bifurcation in the created cross-sectional image 110, as illustrated in FIG. 11. The distance to be calculated here can also be distance 122 that are measured vertically toward reference line 121 as illustrated in FIG. 12.

(Step S94)

Controller 17 calculates the curve in which the distance from a reference to the respective points of the bronchi bifurcation are plotted, using the bronchi spacing distance data as seen in FIG. 13.

(Step S95)

Controller 17 detects whether the form of the bronchi bifurcation is normal or abnormal based on the created curve. Reference 130 is set as seen in FIG. 13, and if created curve 131 runs off to the outside of curve 130 it is determined as a lesion candidate, and when inside of curve 130 it is determined as normal. Practically area ratio r is calculated between the dimension of the framed area by curve 131 that indicates the obtained distance and area 132 being protruded to the outside of area 130. Also threshold T for determining the normal/abnormality of this area ratio r is set in advance. When calculated area ratio r exceeds threshold T it is judged that the form is abnormal, and when area ratio r is less than threshold T it is judged that the form is normal. The reference curve and the threshold here are the quantity that statistically calculated. Threshold T can be set as its option by the input devices of mouse 18 and keyboard 19.

(Step S96)

Controller 17, when the bronchi bifurcation is determined as a lesion candidate, frames the bronchi bifurcation with a circle to highlight on the notable cross-sectional image, for the purpose of drawing attention of the doctor. The style of highlighting can be substituted with color tinting only the bifurcation instead of framing with a circle.

Also, for example, in the case of viewing the bronchi lumen with virtual endoscopy, the affected bifurcation can be displayed in advance with a different color. Color tinting for highlighting can be substituted with the notification through voice or sound at the time the viewpoint of virtual endoscopy passes through the vicinity of the bifurcation. Needless to say both color tinting and voice/sound can be used together.

According to the above embodiment, a lesion candidate formed on the bronchi bifurcation can be detected. This will decrease the burden on the doctor and the patient, and being able to detect the abnormality of the bifurcation in advance will help to avoid the error by oversight in performing the endoscope examination.

The Third Embodiment

Figure 15:
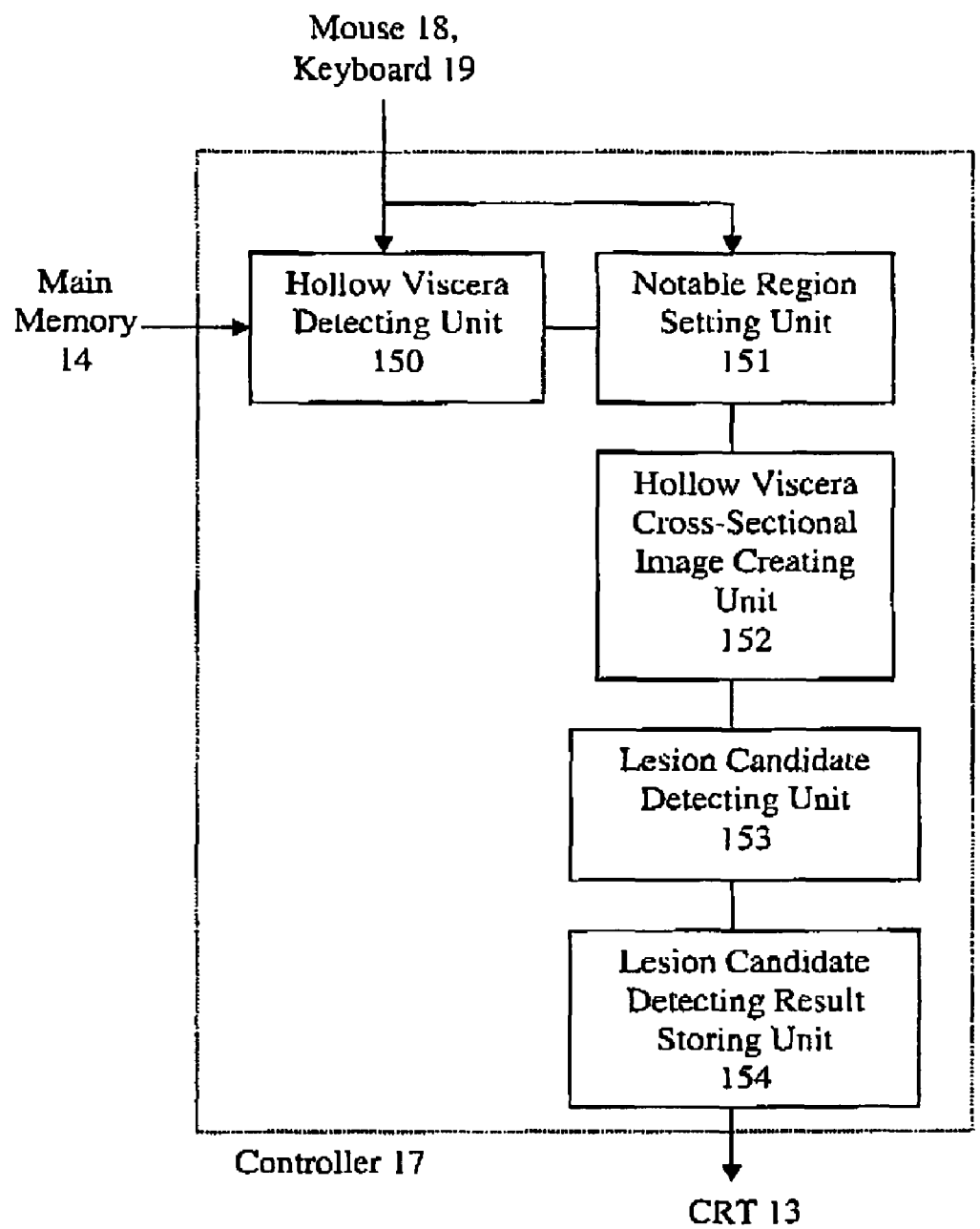
FIG. 15 is a block diagram illustrating the detailed example of the controller in FIG. 1 for explaining the third and fourth embodiments.

FIG. 15 is a block diagram illustrating a detailed example of a controller in FIG. 1 for explaining the third and fourth embodiments.

Controller 17, as illustrated in FIG. 15, includes:

hollow viscera extracting unit 150 being electrically connected to mouse 18, keyboard 19 and main memory 14;

notable region setting unit 151 being electrically connected to mouse 18, keyboard 19 and hollow viscera extracting unit 150;

hollow viscera cross-sectional image creating unit 152 being electrically connected to notable region setting unit 151;

lesion candidate detecting unit 153 being electrically connected to hollow viscera cross-sectional image creating unit 152; and lesion candidate detecting result storing unit 154 being electrically connected to lesion candidate detecting unit 153.

Hollow viscera extracting unit 150 is for extracting the notable hollow viscera from the medical image being inputted from modality 1B via main memory 14.

Notable region setting unit 151 is for setting the region to perform the lesion candidate detecting process corresponding to the hollow viscera extraction results. This setting process can be implemented by operating mouse 18 or other input device as viewing CRT 13 at the discretion of the examiner, or by setting the total extracted region as a notable region.

Hollow viscera cross-sectional image creating unit 152 is for creating the cross-sectional images orthogonal to a long side of the hollow viscera (a direction of the blood vessels and intestinal canals).

Lesion candidate detecting unit 153 is for performing the lesion candidate detecting process to the hollow viscera cross-sectional images being created by hollow viscera cross-sectional image creating unit 152. The lesion candidate detecting process will be explained later referring to FIGS. 17 and 19. Lesion candidate detecting result storing unit 154 is for storing the coordinates of the lesion candidates being detected by the lesion candidate detecting unit, and for displaying them on CRT 13.

Figure 16:
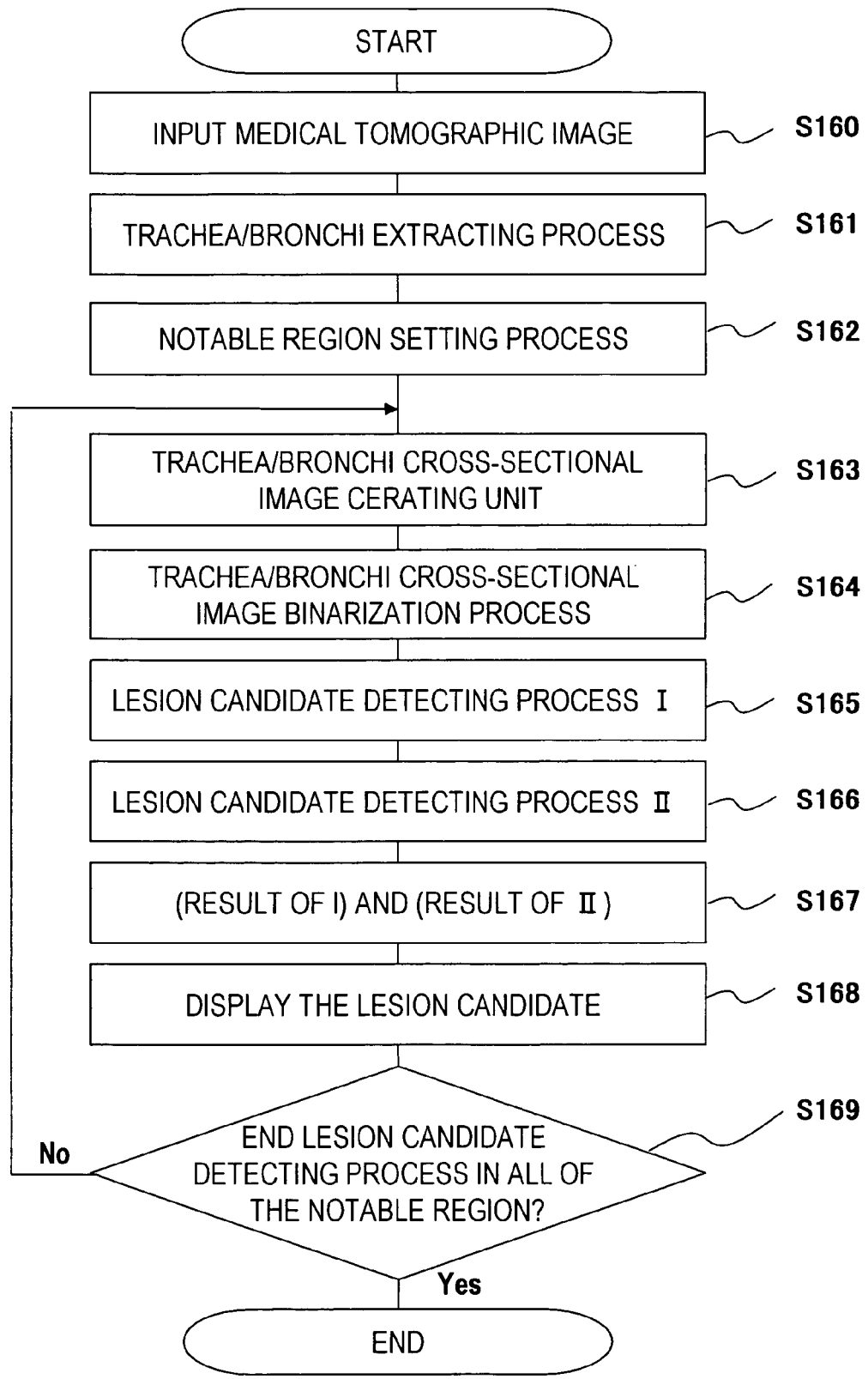
FIG. 16 is a flow chart explaining the operation example of the third embodiment.
Figure 17:
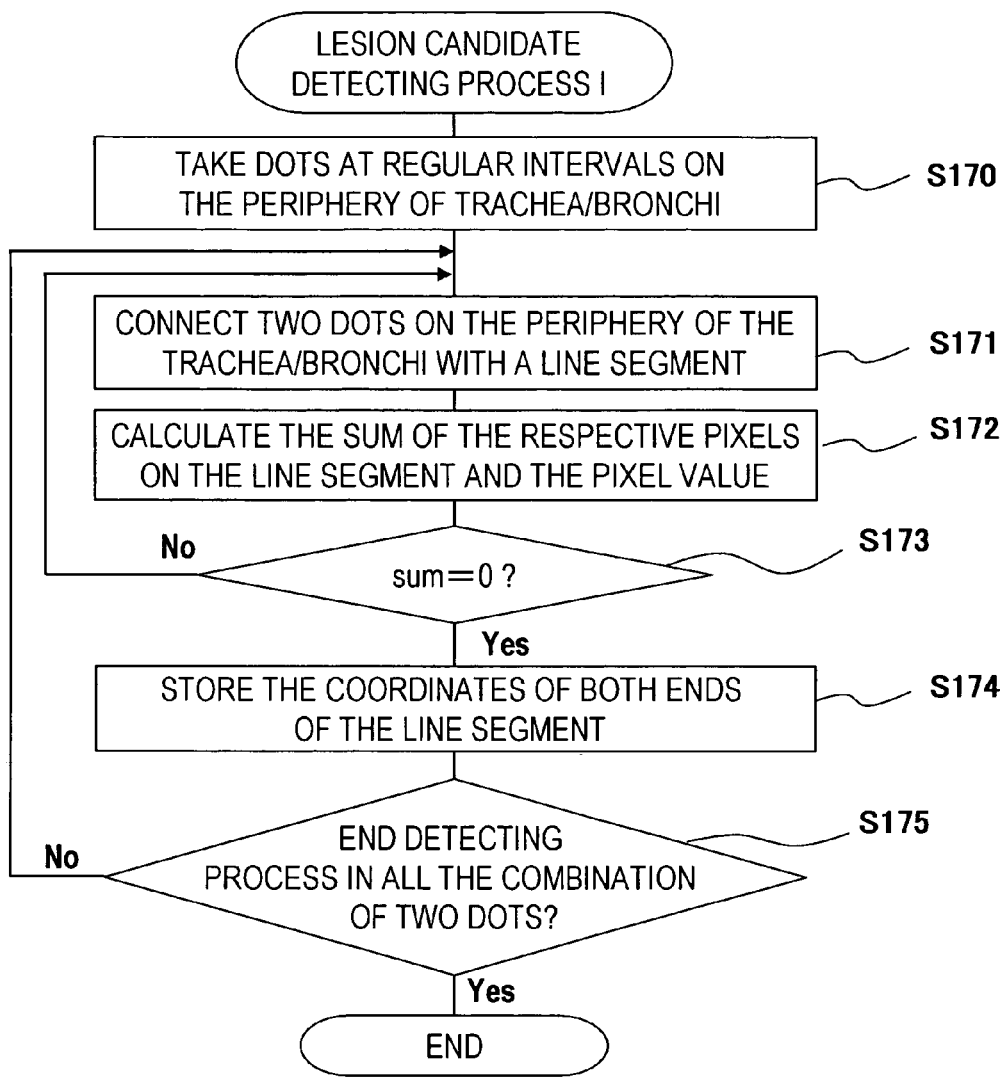
FIG. 17 is a flow chart explaining step S165 in FIG. 16.
Figure 18:
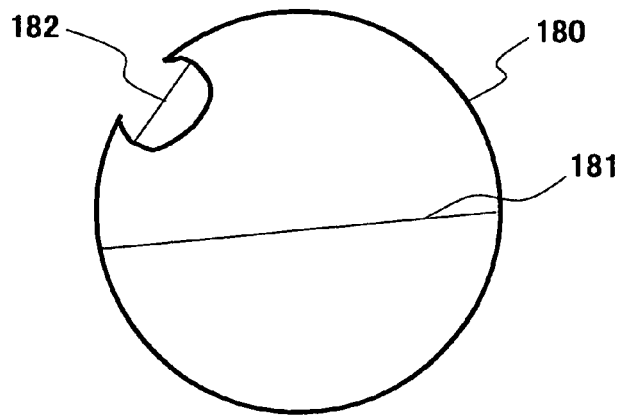
FIG. 18 is a diagram explaining the principle of step S165 in FIG. 16.
Figure 19:
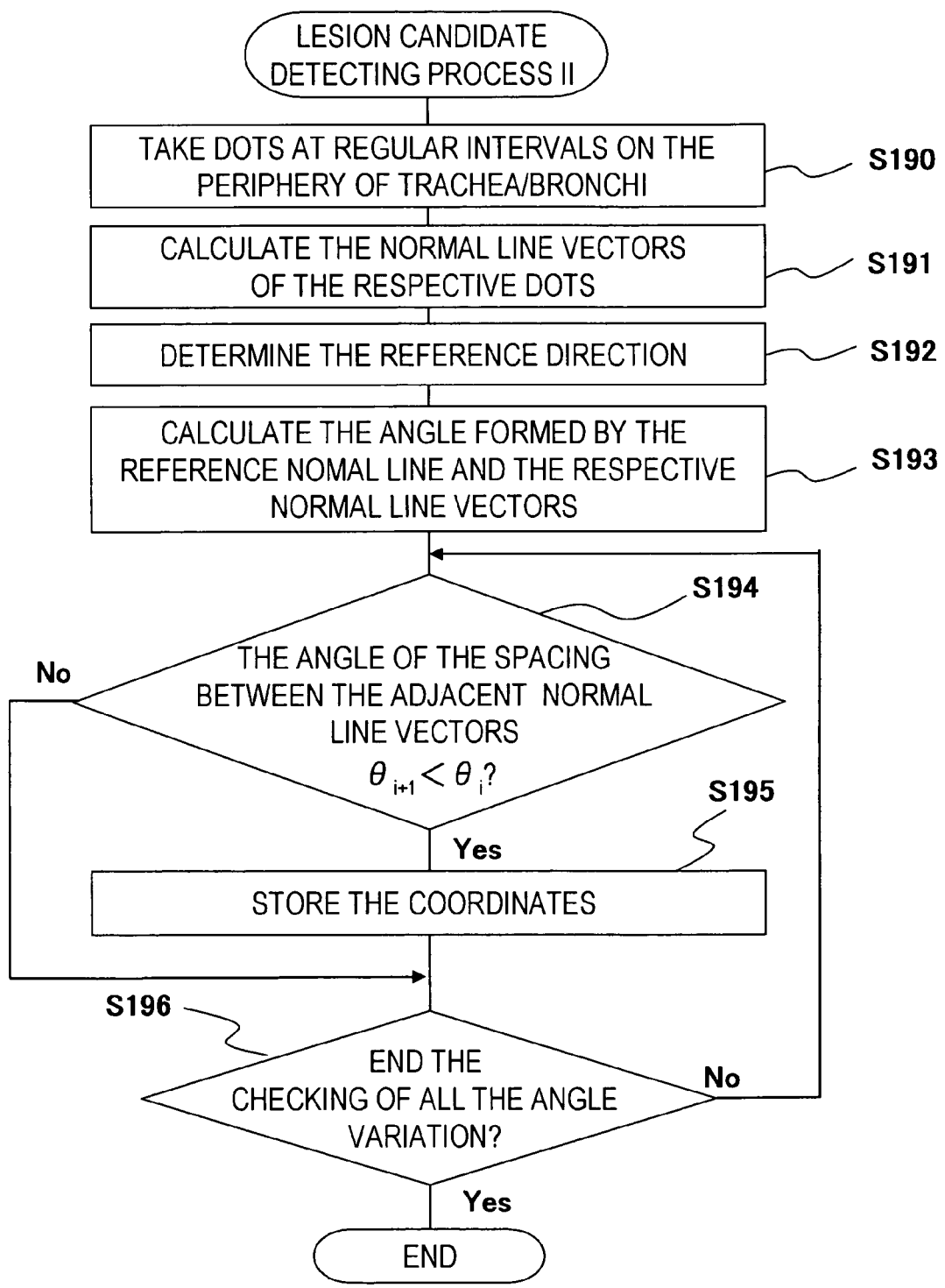
FIG. 19 is a flow chart explaining step S166 in FIG. 16.
Figure 20:
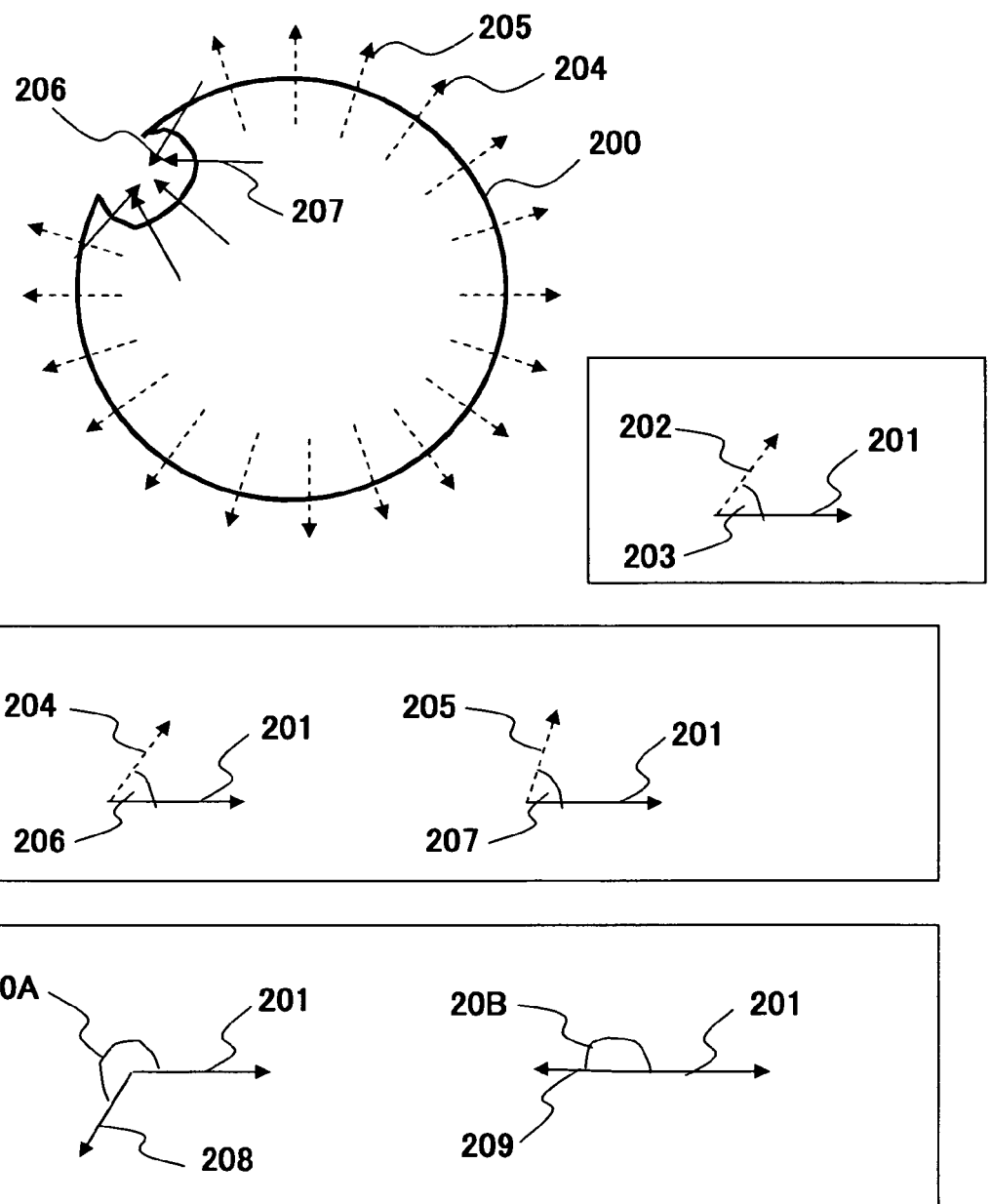
FIG. 20 is a diagram explaining the principle of step S166 in FIG. 16.

Next, the operation of the third embodiment will be explained referring to the drawings. The operation of the third embodiment will now be explained with trachea/bronchi as the example, referring to FIG. 16. FIG. 16 is a flow chart explaining the operation example of the third embodiment, FIGS. 17 and 18 are a flow chart and a principle diagram for explaining step S165 in FIG. 16, and FIGS. 19 and 20 are a flow chart and a principle diagram for explaining step S166 in FIG. 16.

(Step S160)

The operator operates mouse 18 or other input device, and inputs to controller 17 the medical image data being read out from main memory 14.

(Step S161)

Controller 17 extracts the trachea/bronchi region from inputted medical image data. Here, in the case the data in which trachea/bronchi region is extracted is stored in advance in main memory 14 or other memory device, the above-mentioned extracting process can be omitted and the stored data can be inputted to controller 17.

(Step S162)

The operator operates mouse 18, and sets the area to perform the lesion candidate detecting process out of the extracted trachea/bronchi region. The area for setting here indicates a part of or a total trachea/bronchi region.

(Step S163)

Controller 17 makes hollow viscera cross-sectional image creating unit 152 to create the cross-sectional images that are orthogonal to the direction of the trachea/bronchi within the set notable region.

(Step S164)

Controller 17 binarizes the cross-sectional image in relation to the trachea/bronchi area being created by hollow viscera cross-sectional image creating unit 152. This binarization is performed, for example, by allotting pixel value 1 to the pixels of the trachea/bronchi lumen area, and pixel value 0 to the other pixels. In created binarization images of trachea/bronchi area, it is possible to determine that the outline of the trachea/bronchi area will have an oval shape that is almost a circle when normal, and the inside of the oval shape will have a protruding portion when having a protruding lesion such as a tumor or stenosis.

(Step S165)

Controller 17 performs candidate lesion detecting process (I) with regard to binarized trachea/bronchi cross-sectional image.

Candidate lesion detecting process (I) will now be explained referring to FIGS. 17 and 18.

(Step S170)

The operator sets the dots with fixed spacing on the periphery of the trachea/bronchi.

(Step S171)

Controller 17 connects 2 dots out of all the set dots on the peripherals of the trachea/bronchi with a segment line, except the 2 adjacent dots.

(Step S172)

Controller 17 calculates the sum of the pixel value of the respective pixels on the line segment.

(Step S173)

Controller 17 performs the adjudication process to see if the sum of the pixel value is going to be 0 or not.

If sum=0 step S174 is carried out, and if sum<0 or sum>0 it goes back to step S171.

In the case that a protruding lesion exists, out of the line segments that connect any 2 points in the bronchi area 180 of FIG. 18, on line segment 181 which passes the lumen of bronchi, the sum of the pixel value on the line segment turns out as sum<0 or sum>0. On line segment 182 which connects 2 points of the protruding lesion portion, the sum of the pixel value on the line segment turns out as sum=0.

(Step S174)

Controller 17 stores the coordinate, assuming that 2 points at both ends of the line segment of which the sum of the pixel value is sum=0 as being the points on the segment line on the periphery of protruding lesion portion.

(Step S175)

Controller 17 detects if the adjudication process for the sum of the pixel value on the line segment is completed or not, regarding each combination of 2 points on the periphery of the trachea/bronchi area being set in step S171. If not completed it returns to step 171. If completed, the area framed by the coordinates stored in step S174 will be detected as a candidate lesion area.

Lesion candidate detecting process (I) will end as above.

(Step S166)

When lesion candidate detection process (I) ends, controller 17 goes on to perform lesion candidate detecting process (II).

Lesion candidate detecting process (II) will now be explained referring to FIGS. 19 and 20.

(Step S190)

The operator sets the dots with fixed spacing on the periphery of the trachea/bronchi area.

(Step S191)

Controller 17 calculates the normal line vector that is vertical to the tangential line of the periphery of the trachea/bronchi area in the respective points being set with fixed spacing. The direction of the normal line vector here should be aiming from inside to the outside of the trachea/bronchi.

(Step S192)

The operator sets the reference direction vector in the cross section of the trachea/bronchi. The reference direction vector may be set at an arbitrary direction in the cross-section of the trachea/bronchi.

(Step S193)

Controller 17 calculates the angles formed by the reference direction vector and the respective normal line vectors. The calculation of the angle here is, for example, angle 203 being rotated counterclockwise from reference direction vector 201 between reference direction vector 201 being arbitrarily set corresponding to bronchi section 200 and notable normal line vector 202, as illustrated in FIG. 20. Calculation of the angles can of course also be performed clockwise, but needs to be unified either clockwise or counterclockwise in all of the normal line vectors.

(Step S194)

Controller 17 calculates the angular variability from the measured reference direction vector between the adjacent normal vector lines. When the two notable normal line vectors are both of the normal regions, in other words they are on the periphery of the region with no protruding portion in the trachea/bronchi, while viewing normal line vectors counterclockwise like normal line vectors 204 and 205, the magnitude relation of the measured angles would be (angle 206)< (angle 207) and indicates the tendency of increase. On the other hand, if they are of the lesion candidate region, as seen in normal line vectors 208 and 209 the magnitude relation of the measured angles would be (angle 20A)>(angle 20B) and indicates the tendency of decrease. It is possible to detect the lesion candidate from the difference of angular variability. When the angular variability indicates the decrease, step S196 is to be carried out. When it indicates an increase, step S197 is to be carried out.

(Step S195)

Controller 17 stores the coordinate of the segment in which the angular variability is on the decreasing trend as a lesion candidate. Controller 17, in all of the adjacent normal line vectors, goes back to step S194 when the measurement of the angular variability is not completed, and detects the region being framed by the stored coordinates in step S195 as a lesion candidate when completed.

(Step S167)

Controller 17 carries out the logical multiplication of the result from lesion candidate detecting process (I) and the result from lesion candidate detecting process (II). By this calculation only the detected region in both lesion candidate detecting process (I) and (II) will remain, and this remaining region is detected as a lesion candidate region.

(Step S168)

Controller 17 highlights and displays the detected lesion candidate region to CRT 13. The manner of display can be, for example, either circling the lesion candidate region of the trachea/bronchi cross-sectional image, marking with an arrow, or color tinting the region.

(Step S169)

Controller 17 determines whether the lesion candidate detecting process is completed or not in all of the notable regions being set in step S162. If not completed, it goes back to step S163.

According to the above-mentioned embodiment, the protruding lesion being formed in hollow viscera such as trachea/bronchi, blood vessel or intestine can be detected from the medical images such as CT or MR, without using the endoscope or virtual endoscopy.

The Fourth Embodiment

Figure 21:
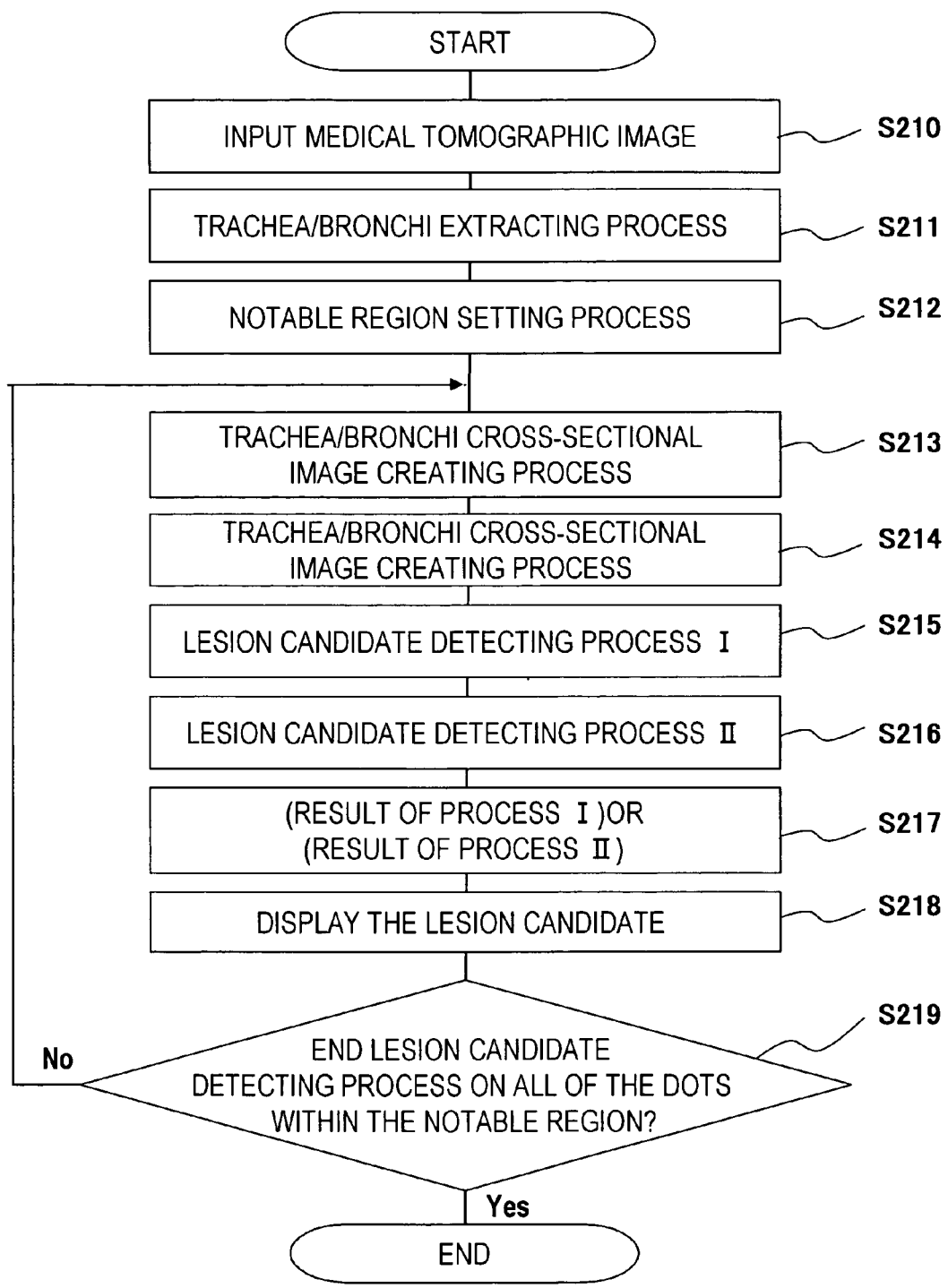
FIG. 21 is a flow chart explaining the operation of the fourth embodiment.

The operation of the fourth embodiment will be explained taking the trachea/bronchi as an example. FIG. 21 is a flowchart explaining the operation of the fourth embodiment.

In the fourth embodiment, similarly as the third embodiment, since steps S160~S166 for creating the cross-sectional images that are orthogonal to the direction of the trachea/bronchi and for obtaining the detecting results of lesion candidate detecting process (I) and (II) are in common with steps S210~S216, the explanation of those common steps will be omitted and only different steps will now be explained.

(Step S217)

Controller 17 performs the logical addition of the detecting result of lesion candidate detecting process (I) and the detecting result of lesion candidate detecting process (II). All of the lesion candidates being detected by this logical addition of lesion candidate detecting process (I) and (II) are obtained as the detection result.

(Step S218)

Controller 17 highlights the lesion candidate region being detected by lesion candidate detecting processes (I) and (II) and displays on CRT 13. Display method can be, for example, either circling the lesion candidate region of the trachea/bronchi cross-sectional images, marking with an arrow instead of circling, or color tinting the region.

Figure 22:
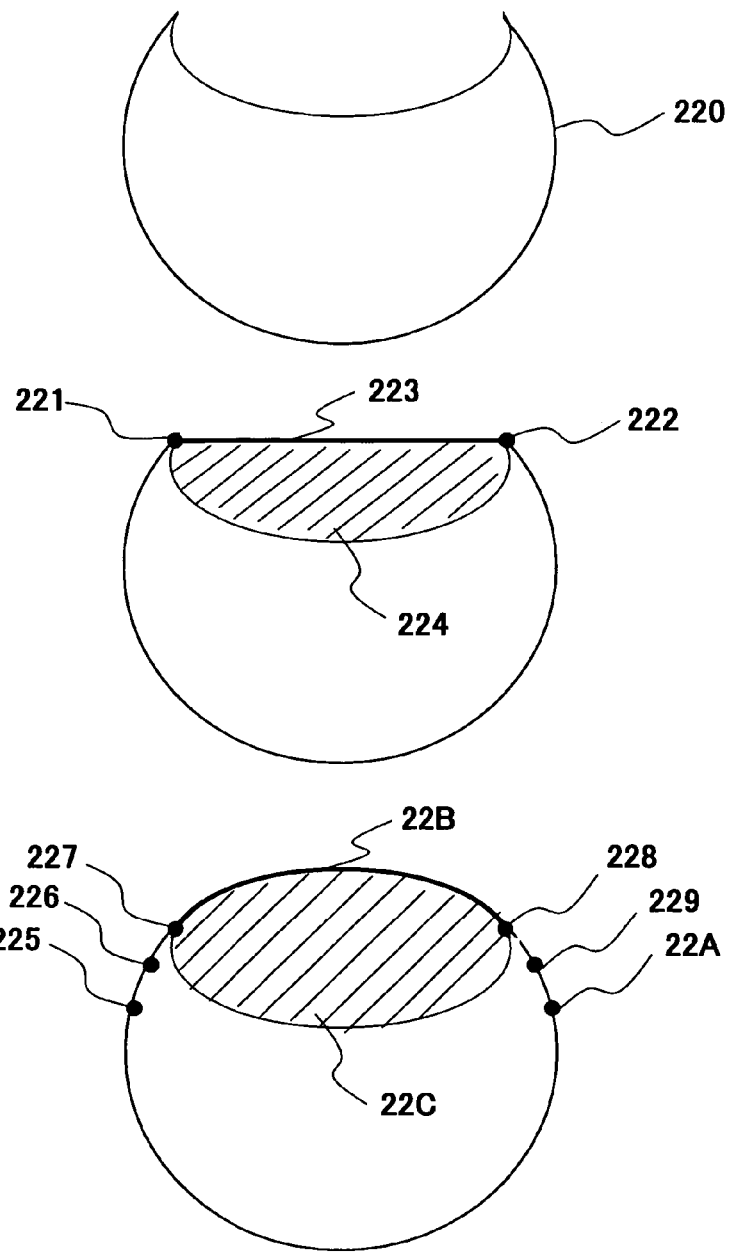
FIG. 22 is a diagram explaining an example of the detecting process of lesion processing.

According to the third and fourth embodiment, after detecting the lesion candidate regions, controller 17 may perform a process to determine the kind of lesion, for example if the lesion is, a polyp or a stenosis. The determining process of the kind of lesion will now be explained referring to FIGS. 22 and 23.

First, controller 17 calculates the outline of the lesion region corresponding to hollow viscera cross-sectional image 220 with a lesion such as a polyp or a stenosis. The outline of the lesion region may be, for example, a line segment 223 connecting lesion region point 221 and 222. In this case the lesion region is 224. Alternatively, the outline of lesion region 22B and lesion region 22C may be obtained by implementing an interpolating process such as the spline interpolation using points 225, 226, 227, 228, 229, and 22A on the outline of the hollow viscera in the vicinity of the lesion region. The method for implementing the spline interpolation using six points are described in FIG. 22, but needless to say the number of points can be set at the discretion of the operator. As described above lesion region 224 or 22C are detected.

Figure 23:
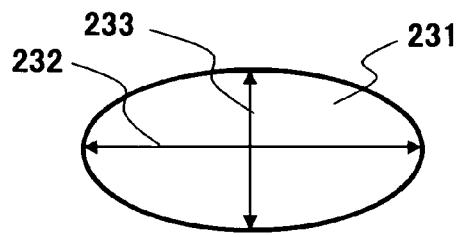
FIG. 23 is a diagram explaining an example of the circularity-degree processing in FIG. 22.

Next, controller 17 calculates how close the detected lesion region is to a circle using the quantum called "degree of circularity" as seen in FIG. 23. Degree of circularity C, for example, can be obtained with formula (1) using dimension S of the lesion region and length R of the periphery:

$$C = 4\pi S/R^2 \qquad (1)$$

The degree of circularity here becomes 1 when it forms a perfect circle, and the more complex the figuration of the lesion becomes the number gets smaller than 1. Thus by setting threshold T, if C>T it will be determined to be a lesion close to a circle such as a polyp, if however C<T it will be determined to be a lesion such as a stenosis.

The above-described degree of circularity can be alternated with a quantum such as the following. Controller 17 calculates long axis 232 (length LL) with regard to lesion region 231 in FIG. 23. The longest line segment here that is orthogonal to long axis 232 out of all the line segments that connect the periphery of lesion region 231 is set as minor axis 233 (length Ls). Controller 17 obtains ratio LL/Ls between the calculated length of the long axis and the minor axis, and determines the lesion to be close to the circle such as a polyp if the ratio corresponding to threshold T is LL/Ls<T. If LL/Ls>T, it is determined to be a lesion such as a stenosis.

Controller 17 may highlight the determined lesion regions according to the kind of lesion as displaying to CRT 13.

Controller 17, for example, circles the lesion with red if it is a polyp, and with blue circle if it is a stenosis, as displaying on CRT 13. Controller 17 may point out the lesion region with a colored arrow instead of a circle, or the lesion region can be color tinted and displayed on CRT 13.

Figure 24:
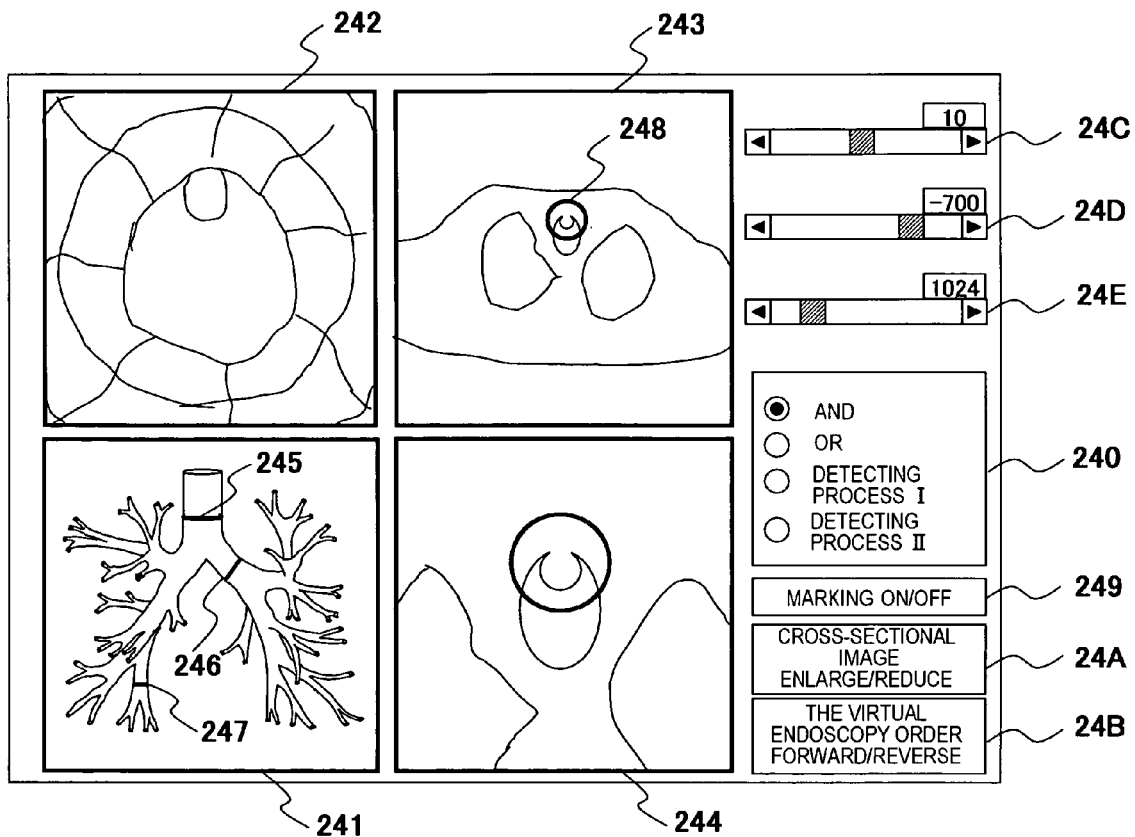
FIG. 24 is a diagram illustrating an example of an image display.

Next, the display method for displaying the result of the lesion region detecting process to CRT 13 which is common in the third and fourth embodiment will be described referring to FIG. 24.

In the third embodiment, the logic multiplication of lesion region detecting processes (I) and (II) is performed. By performing this calculation, diagnostic error by oversight of the lesion region can be decreased.

On the other hand, the logic addition of the lesion region detecting processes (I) and (II) is performed. This enables high-accuracy detection of the lesion region.

Legion region detecting process (I) and (II), as illustrated in the third and fourth embodiment, can be used in combination with logic multiplication or logic addition, or each used independently. The user can choose whether to use these processes as a combination or independently depending on the need such as for higher accuracy or for decreasing diagnostic error by oversight. By using the option display being denoted as 240 in FIG. 24, the operator can freely make a choice of whether to use lesion region detecting process (I) and (II) in combination with the logic multiplication or the logic addition or to use each of them independently. Controller 17 displays images 241~244 as a result according to the method of the lesion candidate detecting process chosen by the operator.

Result image 241 is a 3-dimentional image of the trachea/bronchi being extracted in advance. On the 3-dimentional image, the regions being detected as lesion candidate are displayed with the colored tinted lines 245~247. 3-dimentional images 241 can of course be displayed by rotating with discretional angles.

The operator makes a choice from lesion candidates 245~247 being displayed on 3-dimentional image 241 using mouse 18 or other input devices. The virtual endoscopic image and the cross-sectional image of the chosen lesion candidate region are displayed on display images 242 and 243. Image highlighting process 248 being described in step S168 in the third embodiment and step S218 in the fourth embodiment are implemented on cross-sectional image 243.

It is possible for the operator to select image highlight process 248 whether to display or not by operating mouse 18 and pushing button 249.

The operator can enlarge an image around the lesion candidate in cross-sectional image 243 by operating mouse 18 and pushing button 24A. The magnified view of the image can be displayed in the position of cross-sectional image 243 as it is, or to image display area 244.

The operator also can display either virtual endoscopy image 242 being displayed at the moment (called "forward direction virtual endoscopic image"), and of the opposite direction by rotating 180-degrees. The virtual endoscopic image of the opposite direction can be displayed either in the position of forward-direction virtual endoscopic image 242, or on image display area 244.

Instead of the operator designating the lesion candidate detecting position on 3-dimensional images 121 directly by operating mouse 18, the lesion candidate detecting results can be displayed in order by operating scroll bar 24C. The numeric value being displayed on the numeric display area in the upper part of the scroll bar indicates the number of lesion candidates being displayed at the moment. The number corresponding with the numeric value to be displayed on the numeric display in advance can be displayed in the lesion candidate position on the 3-dimentional images 241, or lesion candidate position 245 corresponding with the numeric value being displayed at the moment in the numeric display area can be presented with lines having different colors from other lesion candidates 246 or 247.

The operator can operate scroll bar 24D and scroll bar 24E by operating mouse 18, and set the window level or window width of cross-sectional image 243. The value of window level or window width to be set is displayed on the numeric display area in the upper part of the respective scroll bars.

Figure 25:
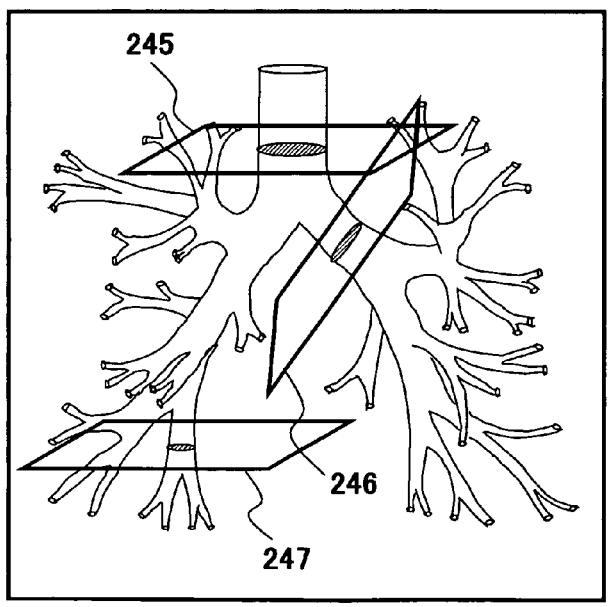
FIG. 25 is a diagram illustrating an example of display variation of image 241 in FIG. 24.

Cross-sections 245, 246 and 247 may be displayed as seen in FIG. 25, instead of colored lines 245~247 indicating the lesion candidate positions being displayed on 3-dimentional images 241.

Also, the same display method can be implemented on the sequential lesion candidate detecting process, lesion kind detecting process and lesion candidate region display, and even on hollow viscera other than trachea/bronchi such as blood vessel or intestinal canal.

According to the above-mentioned embodiment, the protruding lesion formed in the hollow viscera such as trachea/bronchi, blood vessels and intestines can be detected from the medical images such as CT and MR without performing the examination using the endoscope or virtual endoscopy. This will reduce the burden of the doctors and diagnostic errors by oversight of the lesions at the same time.

The Fifth Embodiment

Regarding the lesion candidates being detected in the first~fourth embodiments, the examiner may be indicated of the existence or nonexistence of the lesion in the case of confirming the position, the size and so forth of a lesion using virtual endoscopy.

Controller 17 color tints the lesion region on the virtual endoscopic image being displayed. Also, the examiner, upon viewing with virtual endoscopy as updating the viewpoint, moves the viewpoint toward the lesion right before and after passing through the region portion, and after passing the lesion reverses the viewpoint to the original direction.

Figure 26:
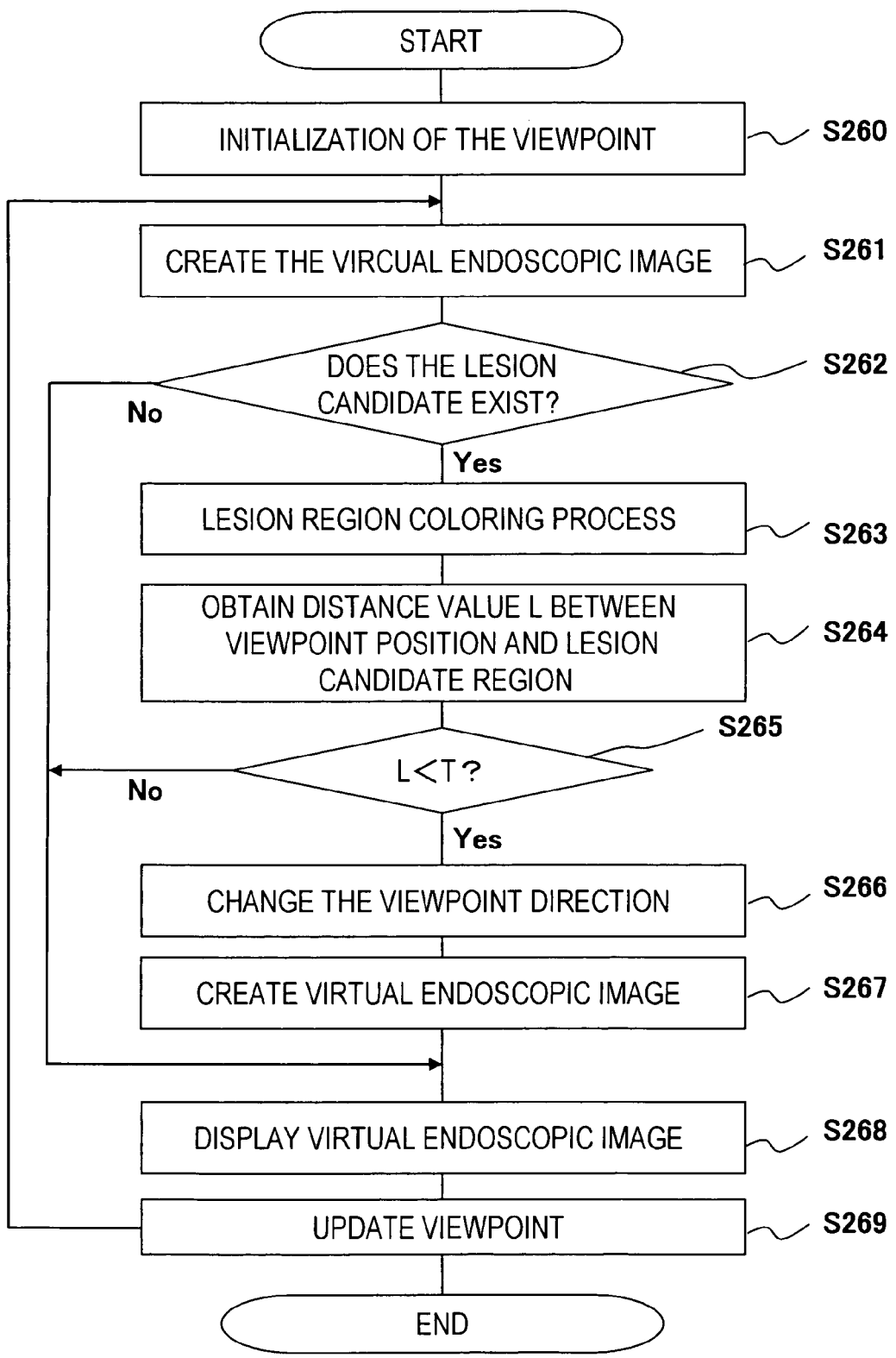
FIG. 26 is a flow chart explaining an operation example of the fifth embodiment.

The fifth embodiment will be explained referring to the diagrams. FIG. 26 is a flowchart illustrating the operation of the present embodiment. Each step will be explained below referring to the diagrams. First the lesion region is detected using one of the lesion detecting methods illustrated in the first~fourth embodiments, and the positional information of those are stored. As creating the virtual endoscopic images by the virtual endoscopic method using the stored positional information, the viewpoint moves forward.

(Step S260)

The operator implements the initialization of virtual endoscopy for the position of the viewpoint. The initialization here means the setting of the starting position for the observation with virtual endoscopy. The setting of the starting position is executed, for example, by the operator clicking one point in the hollow viscera that is the subject for observation on the tomographic images such as CT and MR, using an input device such as mouse 18.

(Step S261)

CPU 11 creates the virtual endoscopic images.

(Step S262)

CPU 11 determines whether the lesion region exists or not in the created virtual endoscopic images, using the information of the lesion being detected in advance by the above-mentioned lesion detecting method. When the lesion region exists, step S263 is carried out, and when the lesion region does not exist, step S268 is carried out.

(Step S263)

Figure 27:
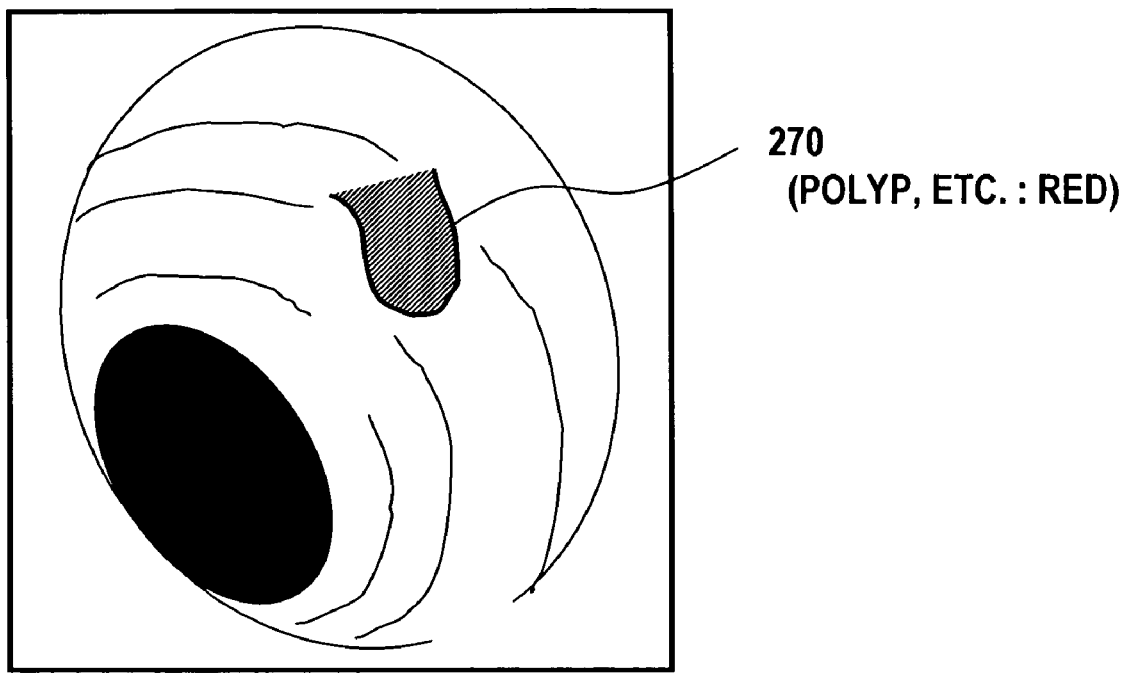
FIG. 27 is a diagram illustrating a display example of the fifth embodiment.

CPU 11 color tints the lesion region on the virtual endoscopic images being created in step S261, for example, as seen in region 270 of FIG. 27.

(Step S264)

CPU 11 measures distance value L between the positions of the viewpoint and the lesion.

(Step S265)

CPU 11 compares the measured distance value L and threshold T being set in advance. When L<T, in other words when the viewpoint is close to the lesion, step S265 is carried out. When L>T, in other words when the viewpoint is far from the lesion, step S268 is carried out.

(Step S266)

CPU 11 shifts the direction of the viewpoint to the direction toward the lesion.

(Step S267)

CPU 11 creates the virtual endoscopic images of the shifted viewpoint.

(Step S268)

CPU 11 displays created virtual endoscopic images to CRT 13 using display memory 12.

(Step S269)

The operator updates the viewpoint of virtual endoscopy. For example, when a left button of virtual endoscopy is held down, the viewpoint moves forward. When the right button is held down, the viewpoint moves backwards. The updating of the viewpoint becomes possible by the above-described operation.

CPU 11, after updating the viewpoint, goes back to S261 and creates the virtual endoscopic images for indicating the existence of a lesion as passing through the lesion region, and displays the created virtual endoscopic images on CRT 13.

The process for color tinting of the lesion region and for directing the viewpoint toward the lesion had been described above. If threshold T is shortened the time for directing the viewpoint is also shortened, the operator is able to detect the lesion without error by oversight because of the quick shift of the viewpoint.

Instead of changing the direction of the viewpoint, the existence of a lesion may be indicated upon passing through the lesion using the change on the virtual endoscopic images by lighting up the whole screen for a moment, by intentionally delaying the updating time of the viewpoint, or by updating the viewpoint in a discontinuous manner. Also, instead of determining whether to execute the visual notification using the distance between the viewpoint and the lesion, the program can be set so that when the lesion occupies more than n % of the viewing field in the virtual endoscopic image, visual notification such as changing the direction of the viewpoint, emission of the screen, delaying the updating time of the viewpoint, or discontinuity of updating the viewpoint would be implemented.

The Sixth Embodiment

Regarding the lesion candidates being detected by the first~fourth embodiment, the methods described below may be implemented for indicating the operator of the existence/nonexistence of a lesion in the case of confirming the position and the size of the lesion using virtual endoscopy.

Figure 28:
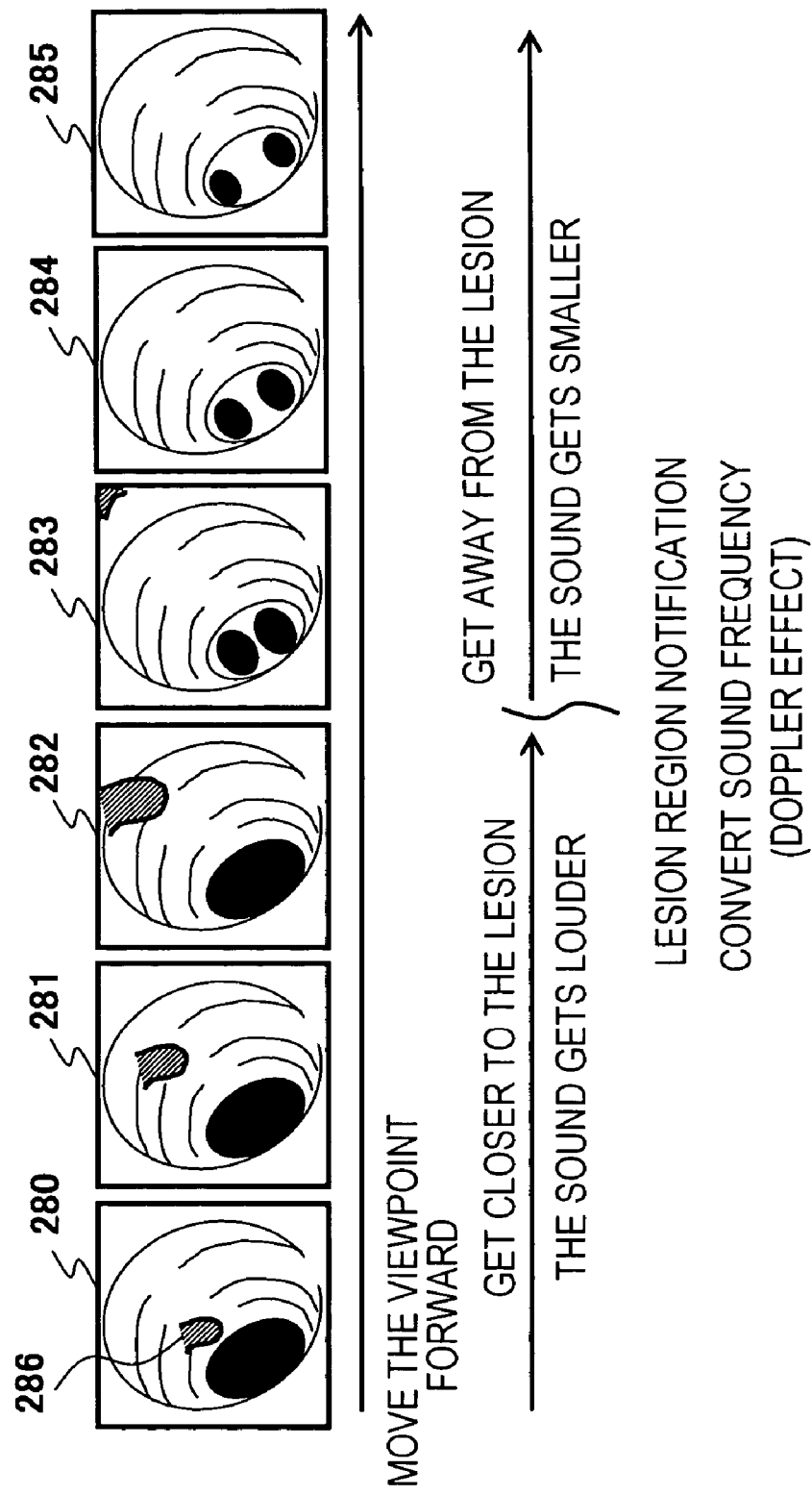
FIG. 28 is a pattern diagram explaining an operation of the sixth embodiment.

The sixth embodiment will be explained referring to the diagrams. 280~285 in FIG. 28 are pictures of observation by virtual endoscopy in the hollow viscera as updating the viewpoint. 286 illustrates a lesion formed in the hollow viscera. The viewpoint is getting close to the lesion in 280~282, passing through the lesion between 282 and 283, and getting away from the lesion in 283~285. A sound is generated when getting close to the lesion. As getting closer to the lesion the sound gets louder, and as getting farther the sound gets smaller. Also when passing through the lesion, the frequency of the sound is converted, and will signals of the passing the lesion to the operator by the Doppler effect.

Figure 29:
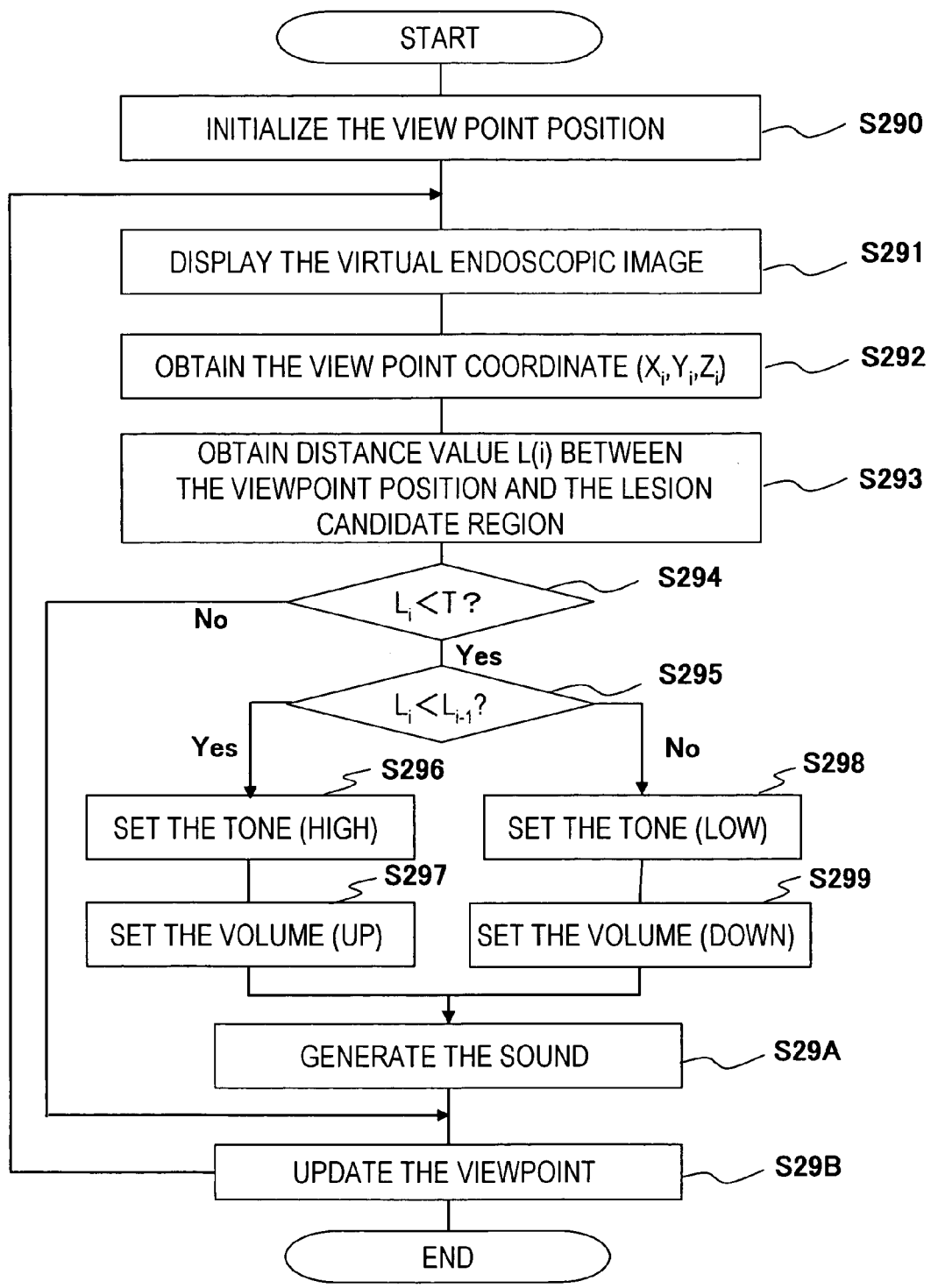
FIG. 29 is a flow chart explaining an operation example of the sixth embodiment.

FIG. 29 is a flowchart illustrating the operation of the present embodiment. Each step will be described below. First, the lesion region is detected using one of the lesion detecting means being illustrated in the first~fourth embodiment, and its positional information is stored. While creating the virtual endoscopic images using the stored positional information, the viewpoint is moved forward.

(Step S290)

The operator executes the initialization of the viewpoint of virtual endoscopy. The initialization here means the setting of the starting position for the examination using virtual endoscopy. The setting of the starting position is executed, for example, by the operator clicking one point of the hollow viscera that is the subject for the examination on the tomographic images such as CT or MR, using an input device such as mouse 18.

(Step S291)

CPU 11 creates the virtual endoscopic images, and stores them on CRT 13 using display memory 12.

(Step S292)

CPU 11 obtains viewpoint coordinates (Xi, Yi, and Zi) at the present time, and stores them in main memory 14.

(Step S293)

CPU 11 obtains distance value Li between the viewpoint and the lesion position, and stores them in main memory 14.

(Step S294)

CPU 11 compares the above-obtained distance value Li and previously set threshold T. When Li<T, in other words when the distance between the viewpoint and the lesion is close, step S295 is carried out. When the distance between the viewpoint and the lesion is far, step S29B is carried out.

(Step S295)

CPU 11 compares the above-obtained distance value Li and distance Li−1 that is the distance between the previous viewpoint and the lesion. When Li<Li−1, in other words when the viewpoint is getting close to the lesion, step S296 is carried out. On the other hand, when Li>Li·1, in other words when the viewpoint is getting far from the lesion, the step S298 is carried out.

(Step S296)

CPU 11 sets the tone interval. When the viewpoint is getting close to the lesion, it is set on high pitch sound. This is for indicating the operator that the viewpoint is passing through the vicinity of the lesion by generating the sound using the Doppler effect by switching the high-pitch sound and the low-pitch sound upon the viewpoint passing through the lesion.

(Step S297)

CPU 11 sets the sound volume. When the viewpoint is getting close to the lesion, the volume is turned up. This is for indicating the operator that the lesion is getting close by the volume being turned up.

(Step S298)

CPU 11 sets the tone interval on low. It indicates that the viewpoint is getting far from the lesion by the Doppler effect.

(Step S 299)

CPU 11 sets the volume of the sound. The volume of the sound is turned low because the lesion is getting far from the viewpoint.

(Step S29A)

CPU 11 generates the sound with the tone interval and the volume being set by the above-mentioned steps S296 and S297 or S298 and S299 through speaker 15.

(Step S29B)

The operator updates the viewpoint of virtual endoscopy. For example, the operator sets the program so that when the left button of the mouse is held down the viewpoint moves forward, and when the right button is held down it moves backwards. It is set so that as the direction of the mouse movement changes so does the direction of the viewpoint. By this updating of viewpoint becomes possible. After updating the viewpoint, the program returns to step S291 again and executes the display of the virtual endoscopic images and the generation of the sound for signaling the existence of a lesion.

In the case where a plurality of lesions exists, a sound with specified tone, rhythm and melody is given to the respective lesions. Also when the lesions are getting close, the existence of a plurality of lesions is indicated to the operator by the generation of a plurality of sounds at once.

As described above, by indicating the operator of the existence and position auditorily using the Doppler effect and the variation of the sound volume, it is possible to decrease the error by oversight of the lesions.

In the fifth embodiment, regarding a protruding lesion formed in the hollow viscera such as trachea/bronchi, blood vessel or intestinal canal, the method for indicating the operator of the position of the lesion region visually in the case of examining the automatically detected lesion region using the virtual endoscopic method was described.

On the other hand, in the sixth embodiment, the method for indicating the lesion region auditorilly was explained. These indicating methods can either be combined or used individually. It is possible to decrease the errors by oversight of the lesions being formed in the hollow viscera such as trachea, bronchi, blood vessel or intestinal canal even in the cases that the operators have short attention spans due to tiredness and such, by combining the various notification methods.

As illustrated in the fifth and sixth embodiments, instead of indicating the operator of the existence/nonexistence of a lesion corresponding to the detected lesion region upon examination using virtual endoscopy, it may be set so that the desired region for observation is stored in advance and when the stored region is getting close it will be indicated visually and auditorily as illustrated in the fifth and sixth embodiments. By this method it is possible to move quickly to the notable region upon using virtual endoscopy. Storing the desired region for observation can be implemented, for example, by clicking mouse 18 on tomographic images such as CT or MR. It also can be done by creating the 3-dimensional images of organs or tissues that are the subjects for observation from the tomographic images such as CT or MR, obtaining the position by clicking mouse 18 on the created 3-dimentional images and storing them.

The Seventh Embodiment

Figure 30:
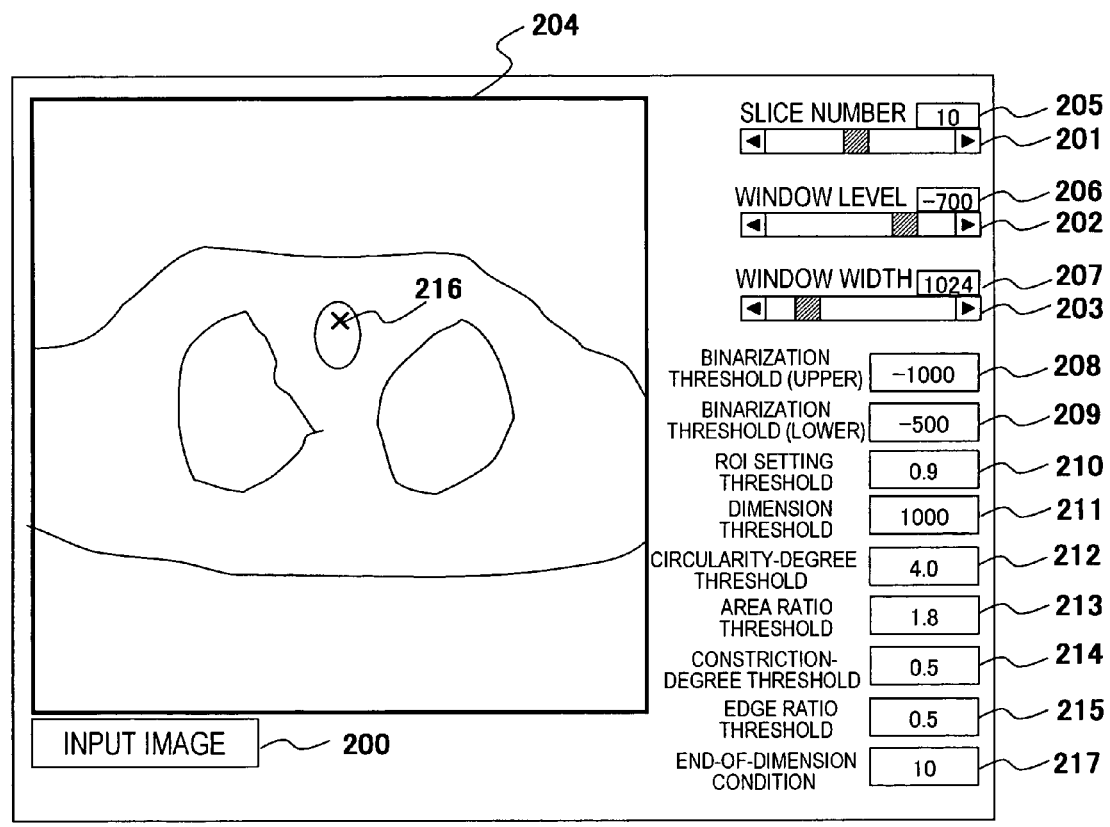
FIG. 30 is a diagram illustrating an example of the medical image display method in the seventh embodiment.
Figure 31:
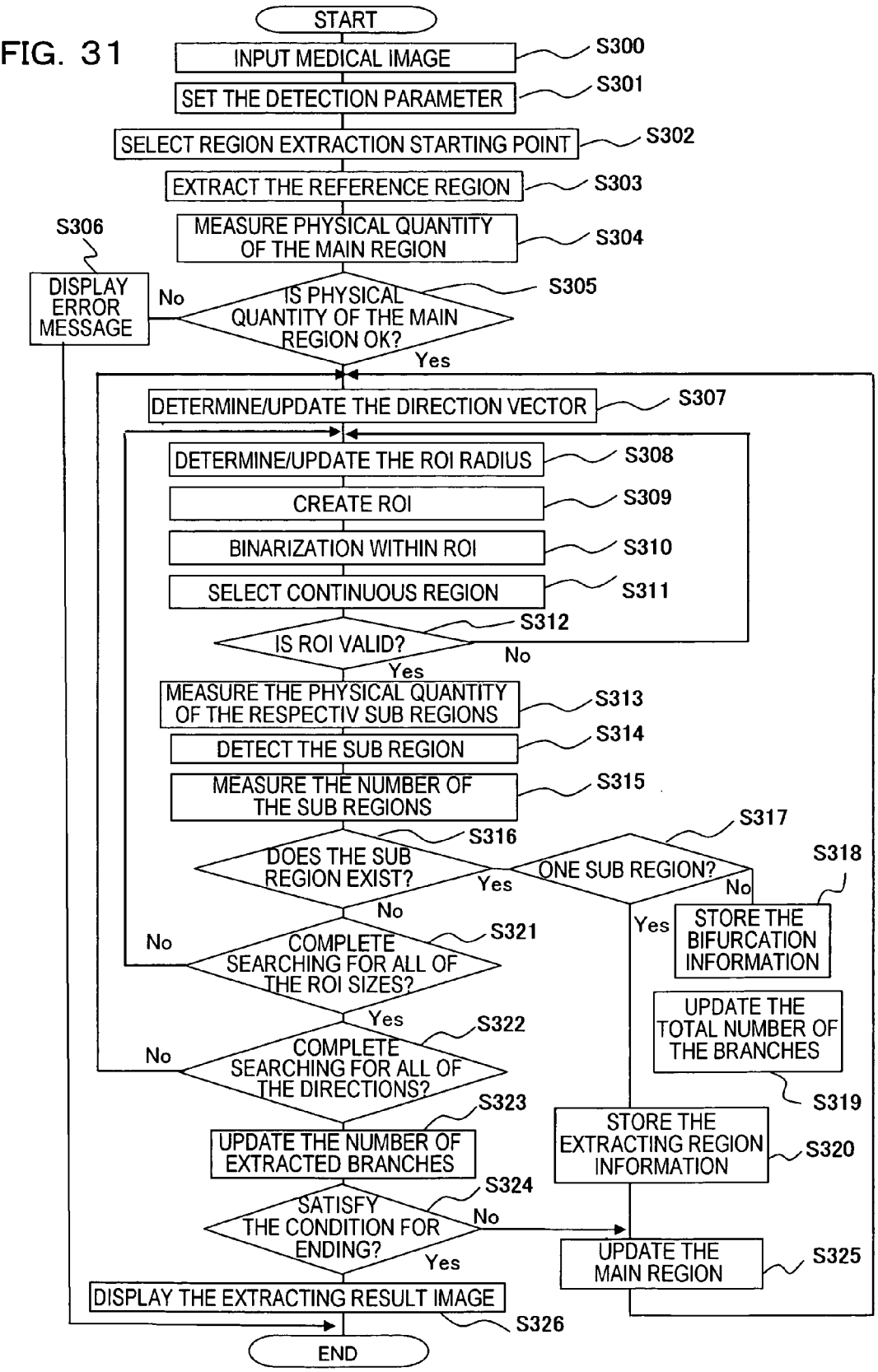
FIG. 31 is a flow chart explaining the operation of the first embodiment in the present invention.

A display example of the present invention is illustrated in FIG. 30. This is a user interface that is common in the seventh~eleventh embodiments to be described below.

A medical image diagnosis support device comprises as illustrated in FIG. 1:

CPU 11 for performing the region extracting calculation;

magnetic disk 16 for receiving the medical tomographic image via networks such as LAN1A and for storing them;

main memory 14 for storing the medical tomographic image data or the intermediate process of calculation upon the region extracting calculation;

mouse 18 or keyboard 19 being connected to controller 17 for inputting the parameters that are necessary for the operators for extracting the regions;

display memory 12 and display device (CRT) 13 for displaying the region extraction results.

Figure 32:
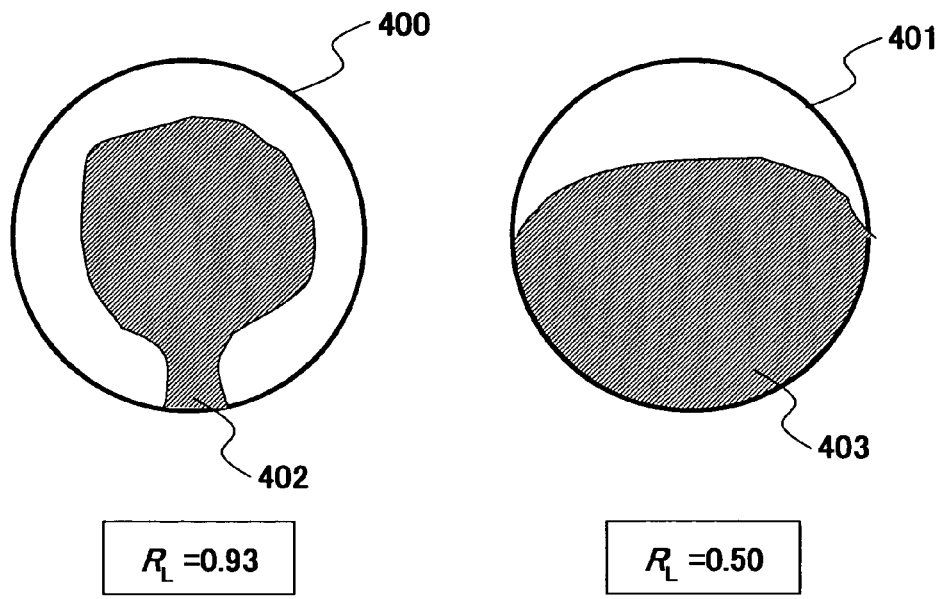
FIG. 32 is an explanatory diagram of step 312 in FIG. 31.
Figure 33:
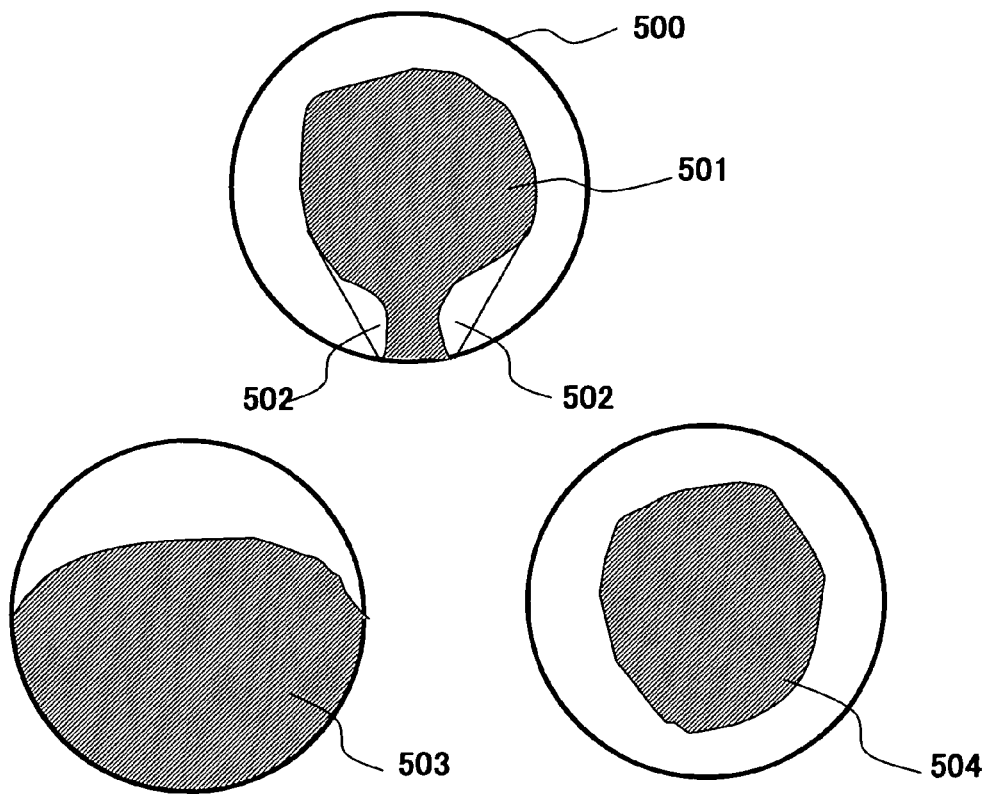
FIG. 33 is an explanatory diagram of step 313 in FIG. 31.

The seventh embodiment of the present invention will be described referring to FIGS. 32~38. FIG. 32 illustrates the process flow of the seventh embodiment.

In the present embodiment, the cross sections that are orthogonal to the direction of the bronchi are being extracted, and then the whole bronchi are extracted by collecting them.

(Step 300)

The operator operates the inputting devices such as mouse 18 or keyboard 19, pushes image input button 200 on the user interface, and inputs the medical tomographic images being imaged by modality 1B to main memory 14 via LAN1A or inputs them from magnet disk 16.

(Step 301)

The operator operates the input device such as mouse 18 or keyboard 19, activates slice number setting scroll bar 201, window level setting scroll bar 202, and window width setting scroll bar 203, and displays desired slice images on image display region 204. The setting of the display slice and the direct input of the value to slice number display region 205, window level display region 206, and window width display region 207 can be executed here. Then the operator sets the value of each parameter to use for extracting the bronchi by operating the input device such as mouse 18 or keyboard 19. Each parameter to use for extracting the bronchi here means, for example, a threshold to use for binarization to be described later, ROI setting threshold, and the dimension threshold, the circularity-degree threshold, the area ratio threshold, constriction-degree threshold, the edge threshold and so forth to use for judging whether the region is extracted correctly or not. The details of each parameter to use for extracting the bronchi will be described later. The setting of the parameters can be implemented by either the operator directly inputting the value to binarization threshold display region 208, 209, ROI setting threshold display region 210, dimension threshold display region 211, circularity-degree threshold display region 212, area ratio threshold display region 213, constriction-degree threshold display region 214, and edge ratio threshold display region 215, or by setting empirically obtained value in advance and using those values. In the case for using the value being set in advance, each parameter value may be displayed on the user interface. Also, the display of each parameter value on the user interface can be omitted.

(Step 302)

The operator operates an input device such as mouse 18 or keyboard 19, and selects a starting point for the region extraction on the arbitrary image out of the inputted medical tomographic images. The starting point for the region extraction here means a desired point on the bronchi on the inputted medical tomographic images, and is set, for example, as point 216 on the image display region in FIG. 30. It is a starting point for executing the usual region extension to use for the next step.

(Step 303)

CPU 11 executes the region extension on the selected arbitrary medical tomographic images based on the set starting point, and extracts the bronchi cross-section on the tomographic images. The bronchi cross-section being extracted here is referred to as a reference region. Pixel value 1 is allotted to the reference region, and pixel region 0 is allotted to the other regions.

(Step 304)

CPU 11 calculates the physical quantity such as dimension value Sp, circularity-degree Cp, gravity-point coordinate Gp, and radius rp at the time of circle approximation of the region. Circulation-degree C. here means, for example, a quantity being given by formula (2), and becomes an index for indicating how close the notable region is to a circle.

$$C=4\pi S/(L \times L) \quad (2)$$

S here is the dimension value of the notable region, and L is the outer circumferential length of the notable region.

(Step 305)

CPU 11 determines whether each of the obtained dimension values of the reference region or physical quantity such as degree of circularity is appropriate as a cross-section of the bronchi. It is assumed that the cross-section that is orthogonal to the direction of the bronchi is an ellipse close to a circle. Thus the degree of circularity comes out close to 1 when measured. Given this factor, the determination of whether the reference region is appropriate for a cross-section or not is executed by comparing each set of threshold and obtained physical quantities, and seeing if each physical quantity meets the conditions set by the thresholds. When there is even one physical quantity that does not meet the condition, step 306 is carried out, and when all of the physical quantity meets the condition, step 307 is carried out.

(Step 306)

In the case that the reference region is judged as inappropriate, the hollow viscera extracting process ends by outputting the error message.

(Step 307)

CPU 11 decides or updates the direction vector for extracting the next cross-section of hollow viscera. A point transferred by a unit length toward the updated direction vector from reference region gravity point Gp, is set as the tentative center O of the region for the next extraction.

(Step 308)

CPU 11 determines radius R of the region of interest (hereinafter referred to as ROI) for extracting the region. Radius R here is the fixed number of times as the radius (or the long axis length of the rectangle framing the reference region) r. ROI converts the radius within the predetermined range until the proper one is found, as described later on. The proper ROI will be described later. The predetermined range is, for example, the range being presented as ar<R<br using the reference region radius r. Here a and b is a ratio being predetermined in advance. In concrete terms it is set, for example, as a=0.6, b=1.4. R is increased, for example, at 0.2r intervals from 0.6r to 1.4r until the proper ROI is found.

(Step 309)

CPU 11 sets ROI of radius R being orthogonal to the direction vector with set tentative center O as a center, and creates the images in the ROI using the input medical tomographic images. In addition, CPU 11 calculates the interpolation on the spacing of the faults of the input medical tomographic images for allotting the pixel value to the respective pixels in ROI.

(Step 310)

CPU 11 binarizes using the set threshold of binarization corresponding to the obtained images in the ROI. CPU 11 allots here pixel value 1 to the lesion candidate of the bronchi that meets the threshold condition, and allots pixel value 0 to the other region.

(Step 311)

Out of the respective regions in the binarization images, leaving only the region being connected with the reference region, CPU 11 allots pixel value 0 to the other regions.

(Step 312)

CPU 11 determines whether set ROI is appropriate or not. As seen in FIG. 32, the case that bronchi lesion candidate 401 is obtained and the case that bronchi lesion candidate 402 is obtained by binarization are considered. The length of the circumference of ROI 440 and ROI 401 are set as LROI, and the length of the part out of the periphery that are not adjoining bronchi lesion candidate regions 402 and 403 being obtained by the binarization are each set as L402 and L403. When proportion RL of LROI which is the periphery length of ROI and L402 and L403 which are the length of the part out of the periphery that are not adjoining bronchi lesion candidate turns out to be RL>TROI when compared with ROI set threshold TROI which is one of the set region detecting parameters, set ROI is determined as appropriate and step 313 is carried out. And when it turns out to be RL<TROI it is determined that set ROI is inappropriate and the process returns to step 308. For example, if TROI is set as TROI=0.7, ROI400 is determined as appropriate and ROI401 is determined inappropriate.

(Step 313)

Figure 34:
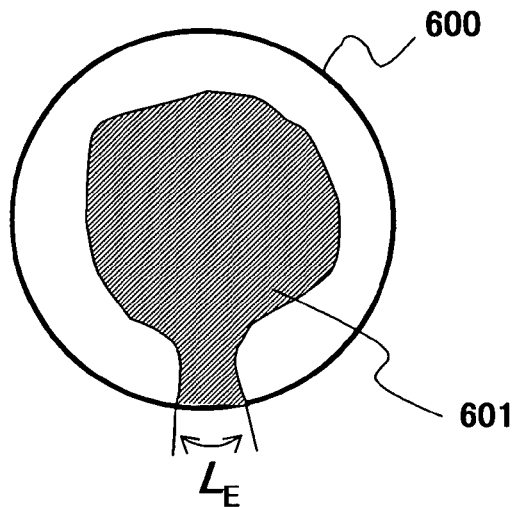
FIG. 34 is an explanatory diagram of step 313 in FIG. 31.
Figure 35:
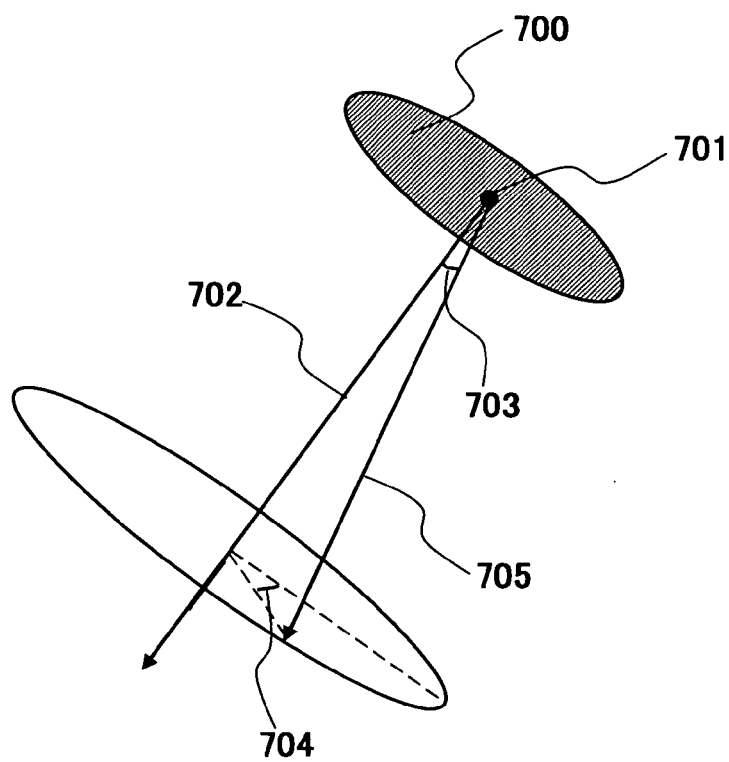
FIG. 35 is an explanatory diagram of step 322 in FIG. 31.

CPU 11 calculates dimension Sc or degree of circularity Cc of the bronchi lesion candidate region (hereinafter referred as sub region candidate), RS which is an area ratio comparing with the reference region, degree of deformation (degree of constriction) W, edge ratio E, gravity point coordinate Gc. The degree of constriction here is the quantity represented as W=Sw/Sc using dimension of sub region candidate Sc when the dimension of constricted part 502 out of sub region candidate 501 in ROI 500 is set as Sw as illustrated in FIG. 35. When the constricted part does not exist as region 503, the degree of constriction is represented as W=0. However in the case there is no part that adjoining the periphery, the degree of constriction is represented as W=1. Also, the edge ratio is, as seen in FIG. 34, with the length of the part that the periphery of ROI600 and sub region candidate 601 is tangent being set as LE and using the length of periphery LROI of ROI600, the quantity represented as E=LE/LROI.

(Step 314)

CPU 11 compares the calculated physical quantity such as dimension of sub region candidate Sc, degree of circularity Cc, Rs which is an area ratio comparing with the reference region, degree of constriction W, and edge ratio E and respectively set region extracting parameters, and determines whether it is appropriate as to the bronchi region or not. The region extracting parameters used here are dimension threshold TS, circularity-degree threshold TC, area ratio threshold TR1 (lower side), TR2 (upper side), constriction-degree threshold TW, and edge ratio threshold TE. Dimension threshold TS is to use in the case the size of the region that is not appropriate as cross-section of the bronchial region is found, for eliminating that region. Area ratio threshold TR1 and TR2 are the parameters to compensate for the persistence with the reference region. The constriction-degree threshold is, for example as seen in region 503 in FIG. 33, in this case a part of the lung region are extracted as a sub region candidate, for excluding them. The edge ratio is the same as the degree of constriction. In the case that all of these physical quantities meet the threshold condition, the sub region candidate is selected as a cross section for the bronchi region. The selected sub region candidate is referred as a sub region. Pixel 0 is allotted to the sub region candidate not being selected as the cross section for bronchi region. To determine whether the sub region candidate is appropriate as the cross section for bronchial region or not may be determined by using all of the previously mentioned physical quantities, or a part of the physical quantities.

(Step 315)

CPU 11 counts the number of the sub regions being determined as appropriate as a bronchial region by the sub region candidate detecting process of step 314.

(Step 316)

CPU 11 determines whether the obtained number of the sub region is 0 or not, and if the sub region is not 0 step 317 is carried out. If the sub region is 0 step 321 is carried out.

(Step 317)

CPU 11 determines whether the number of the obtained sub region is one or more than two, and when the number of the sub region is more than two, step 318 is carried out. When the number of sub region is one step 320 is carried out.

(Step 318)

When the number of the sub region is two or more, CPU 11 determines that it is the bronchi bifurcation, and stores the respective parameters of gravity-point coordinate Gp of the reference region, dimension Sp, degree of circularity Cp, the coordinate of the respective pixels in the reference region, direction vector, and radius R of ROI and so forth at the time in the bifurcation information storing sequence on main memory 14.

(Step 319)

CPU 11 increases bronchial branch account Nt only by (number of sub regions·1). Bronchial branch account Nt is a total number of bronchial branches, and for completing the whole bronchi extracting process when the extracting process is finished in all of the branches of the whole bronchi.

(Step 320)

CPU 11 stores the coordinate of the respective pixels in the extracted sub region to the extracting region coordinate storing arrangement.

(Step 321)

When the sub region is not extracted, CPU 11 creates ROI on all the ROI radiuses, determines whether the extracting process of the sub region candidate is executed, and if extracting process is completed on all of the ROI radiuses, step 322 is carried out. When ROI is not created in all of the ROI radiuses, CPU 11 returns to step 308, updates ROI radius, and executes extracting process.

(Step 322)

CPU 11 determines whether the extracting process is executed on the direction vector of all the angles, and when the extracting process is completed with the direction vector of all the angles, step 323 is carried out. When the extracting process is not completed on all of the direction vectors, it returns to step 307 and updates the direction vector. The meaning on all of the direction vectors will now be explained. As illustrated in FIG. 35, vector 705 being defined by angle 703 and 704 corresponding to vector 702 which is orthogonal to the reference region from gravity point 701 of reference region 700 is obtained. Vectors 705 that are possible to be obtained in all of the combinations in which angles 703 and 704 can obtain, are all of the direction vectors. In a practical sense, for example, angles 703 and 704 can respectively be obtained from 0° to 360° at 10° intervals, or at 5° intervals. Also, it may be that angle 703 is obtained at 5° intervals, and angle 704 is obtained at 10° intervals. Or, it may be that angle 703 is obtained from 0° to 90°, and angle 704 is obtained from 0° to 360°.

(Step 323)

CPU 11 increases the value of extracted branch account Nf by 1. Extracted branch account Nf indicates the number of branches in which the extracting process is completed out of each branch of the bronchi.

(Step 324)

CPU 11 compares the extracted branch account Nf and total branch account Nt. In the case of Nf<Nt, step 325 is carried out. In the case of Nf=Nt, step 326 is carried out.

(Step 325)

CPU 11 sets gravity-center coordinate Gc, dimension Sc, and circularity-degree Cc of the sub region being extracted in step 314 as the new reference region gravity-center coordinate Gp, dimension Sp and circularity-degree Cp, returns to step 307 and repeats the extracting process. In the case the sub region is not extracted in step 314, CPU 11 obtains the reference region information from the bifurcation information storing arrangement, and starts the extracting process of another branch from the one that had been receiving the extracting process up until that moment.

(Step 326)

Figure 36:
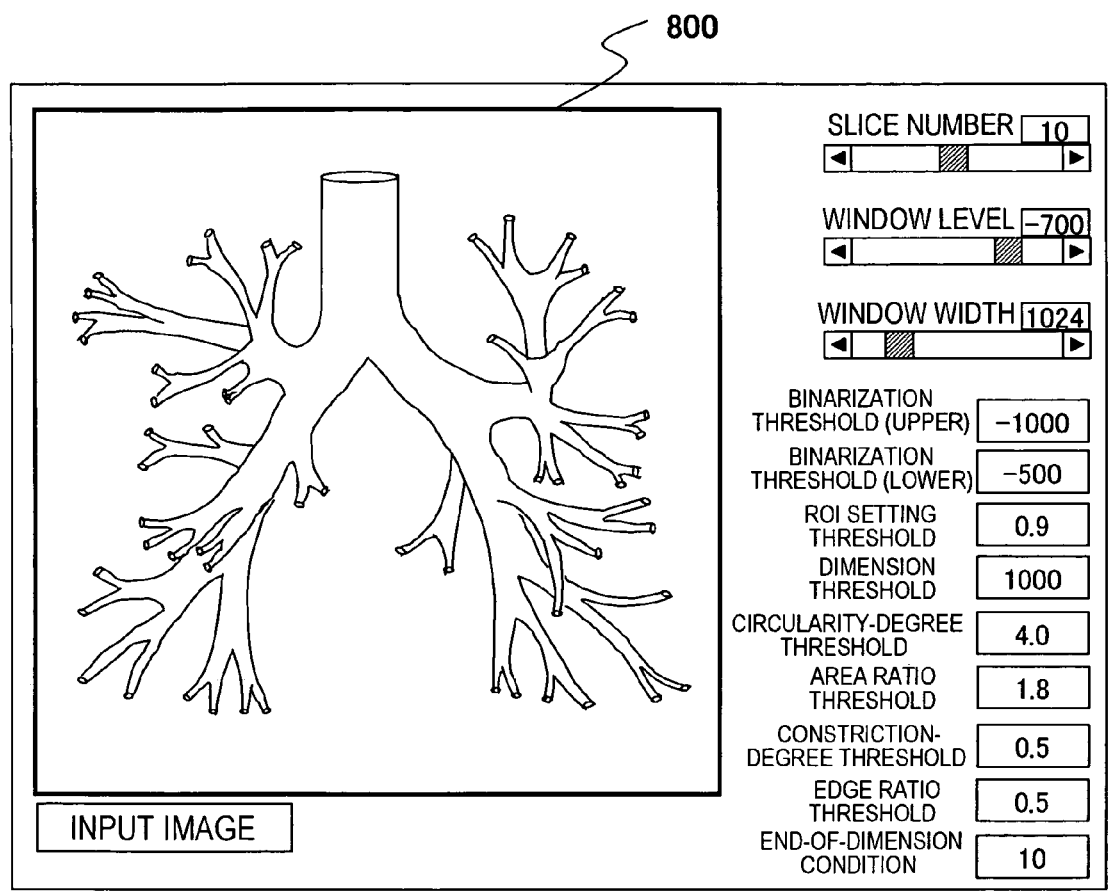
FIG. 36 is a display example of the extraction result in the seventh embodiment of the present invention.

CPU 11 creates the 3-dimentional images of the bronchi being extracted on the basis of the information being stored in the extracting region information storing arrangement, and displays it on the indicator using the display memory. Extracted bronchi 3-dimentional images are displayed, for example, on image display region 800 on the user interface as illustrated in FIG. 36.

Figure 37:
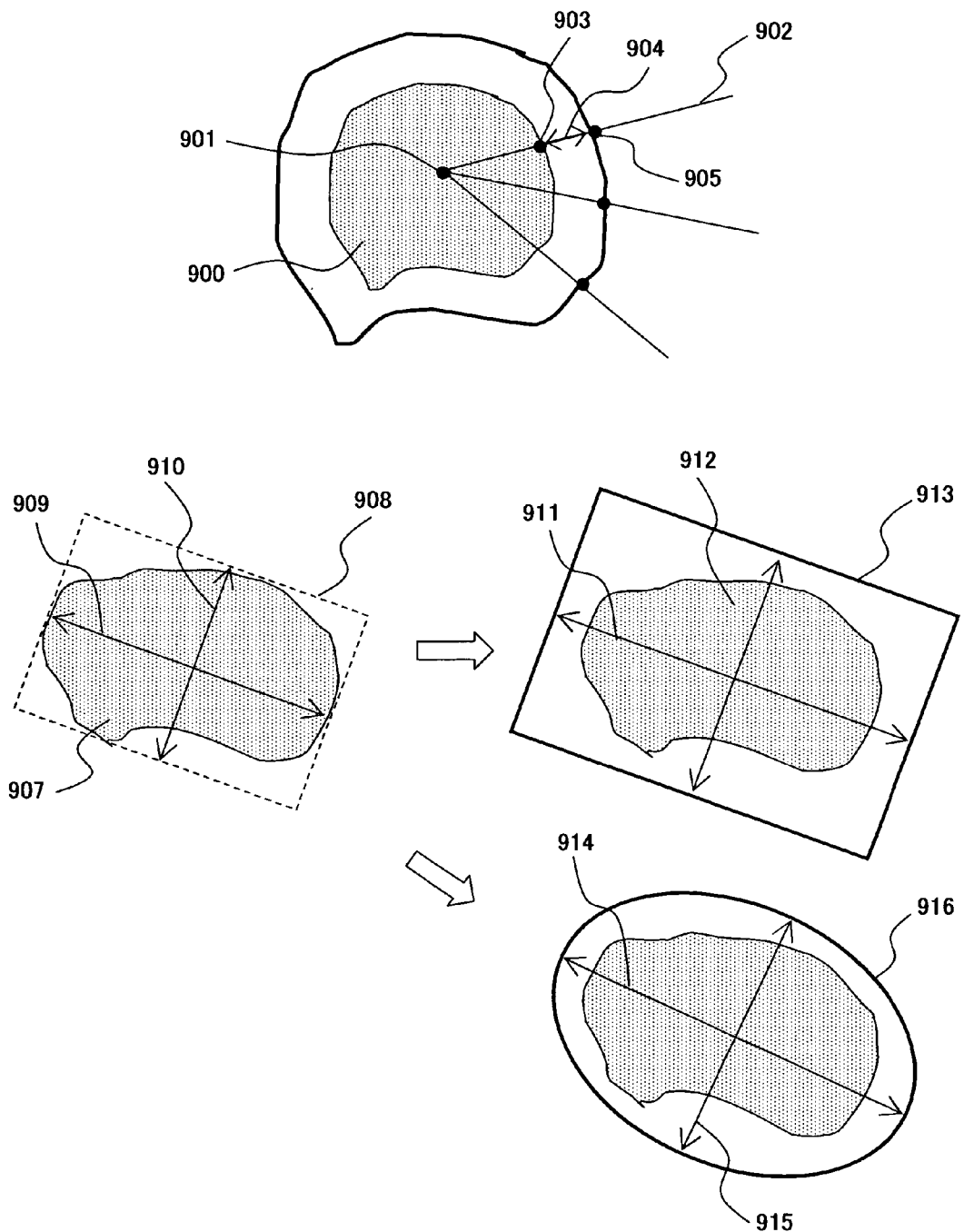
FIG. 37 is a diagram illustrating various ROI forms.

Above-described is one of the embodiments of the present invention. ROI of a circle is used here, but ROI other than the circle may be used. For example, as illustrated in FIG. 37, straight line 902 is drawn from gravity-point 901 of reference region 900 to the outside. Point 905 is taken on the straight line that is away by fixed distance 904 from point 903 in which the straight line 903 crosses the periphery of the reference region. Line 906 connecting the point group obtained by rotating straight line 902 by 360° with reference region gravity-point 901 as supporting point may be set as the periphery of ROI. Distance 904 here is set at discretional measurement by step 321.

Or, rectangular region 908 that frames reference region 907, and the long side 909 and short side 910 are obtained. Then rectangular region 913 that has long side with length of 911 and the short side with length of 912 being obtained by multiplying each of the length 909 of the long side and the length 910 of the short side of rectangular region 908 by, may be obtained and set as ROI. Or an ellipse that has long axis 914 and short axis 915 that are a times length each of the long side 909 and short side 910 of rectangular region 908 may be obtained, and set as ROI.

Though the case for fixing ROI setting threshold TROI for using to determine whether ROI is appropriate or not into the steady value was described here, it is possible to convert ROI threshold into a variable. Hereinafter the case for the variable ROI setting threshold will be described.

As executed in the process of step 322, direction vector 702 which is orthogonal to the reference region from gravity-point 701 of reference region 700 in FIG. 35 as the reference direction vector, ROI is created as a varying angle 703 from reference direction vector 702. ROI setting threshold, for example, may be varied at this point, by every angle 703. Variable ROI setting threshold will now be explained using FIG. 38.

The operator gives lower limit value TROI1 and upper limit value TROI2 of the ROI setting threshold. These values may either be set so that the operator can directly set them on the user interface, or keeping the values that are set inside in advance.

For example, as illustrated in FIG. 38, in the case of varying the angle from reference direction vector 1000 from 0° to angle 1001, TROI1 is given to the reference direction vector as the ROI setting threshold, and TROI2 is given to the direction vector 1002 being tilted by the angle of 1001. The extraction order of the respective bronchial branches in the seventh embodiment is illustrated in FIG. 39.

Figure 39:
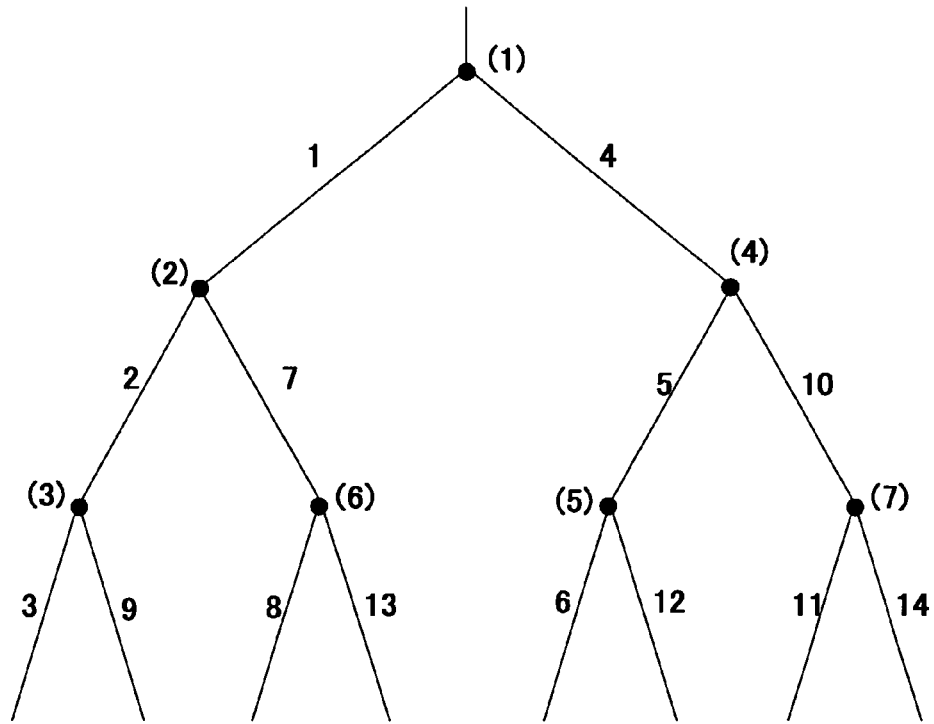
FIG. 39 is a diagram presenting the extraction order of the bronchial branch and the bifurcations being extracted by the seventh embodiment of the present invention.

Suppose that the bronchi is a tree-structured chart illustrated in FIG. 39, and that the extraction is executed from top to bottom of the tree structure. In the seventh embodiment, when the bifurcation is reached, the bifurcation is stored and further extraction is to be carried out toward the bottom. Suppose in the bifurcation that the branch on the left side is extracted preferentially. When the branch in the middle of extracting reaches the bottom, it returns to the bifurcation being stored the earliest out of all the stored bifurcation information, and carries out the extraction on the branch of the other side from the one extracted earlier. In other words, even upon reaching the bifurcation the extraction would not stop, and when the extraction is completed at the lowest part of the branch, the extraction stops there and proceeds on to another branch.

FIG. 39 illustrates by number in what kind of order the extraction takes from the bifurcation to bifurcation. Also, the numbers that are circled illustrates in what kind of order the extraction takes in each bifurcation.

By setting angle 1001 as θ max, ROI setting threshold value TROI (θ) of the direction vector 1003 that is tilted by angle θ from the reference direction vector, may be given with the formula (3).

$$TROI(\theta) = TROI1 + (TROI2 - TROI1) \times \sin\theta / \sin\theta\max \quad (3)$$

Or, angle 1001 may be set as θ max, to give ROI setting threshold TROI (θ) of the direction vector 1003 the formula (4) as follows:

$$TROI(\theta) = TROI1 + (TROI2 - TROI1) \times \theta / \theta\max \quad (4)$$

Also to all of the direction vectors of which the angle θ from the reference direction vector turns out to be θ>θ1, ROI setting threshold TROI2 may be given, and ROI setting threshold may be determined by formula (3) or (4) in a range of 0<θ<θ1. It should be set as θ max=θ1 at this point.

ROI setting threshold may be determined by making it proportional to reference region dimensional value Sp. The operator gives the lower limit value TROI1 and upper limit value TROI2 of the ROI setting threshold. These values may be such that the operator can either directly set them on the user interface, or can maintain the values being set inside in advance.

For example, the ROI setting threshold value, when the reference region dimension value is Sp<S1, is set as TTROI2. When the reference region dimension value is S1<Sp<S2, ROI setting threshold value TROI(Sp) may be set as formula (5).

$$TROI(Sp) = TROI1 + (TROI2 - TROI1) \times (Sp - S1)/(S2 - S1) \quad (5)$$

S1 and S2 here may be either given by the operator or maintained inside in advance. It is possible to speed up the calculation of ROI setting threshold TROI being given by the above mentioned formulas (4) or (5), by calculating them in advance using the above-mentioned formulas (4) or (5) and creating the reference table. Also, ROI setting threshold TROI being obtained by experience without using the above-mentioned formulas (4) or (5) may be added into the reference table.

The Eighth Embodiment

Figure 40:
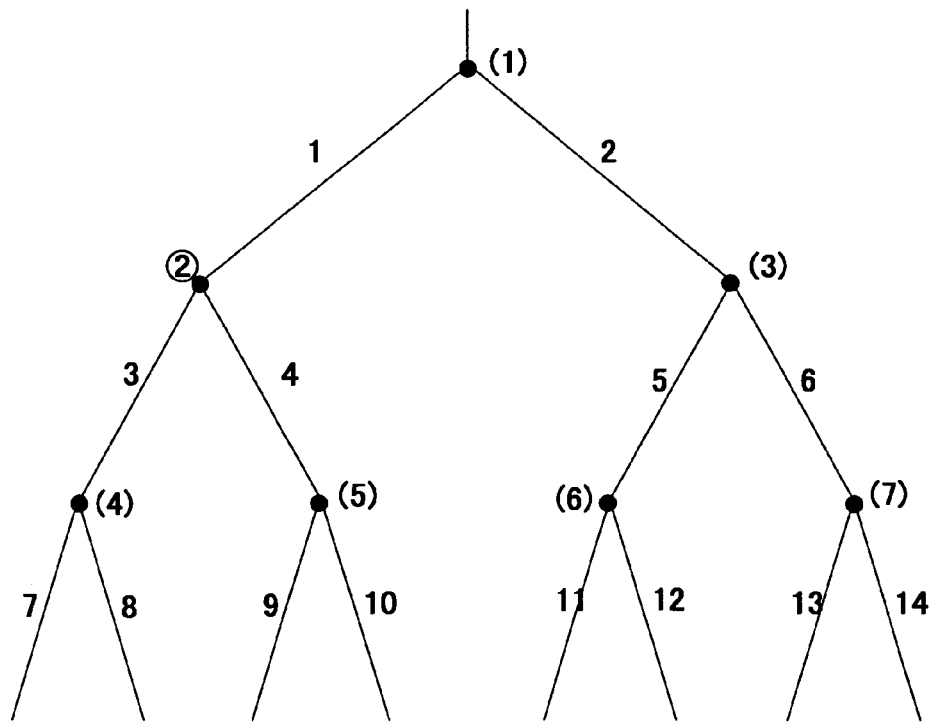
FIG. 40 is a diagram presenting the extraction order of the bronchial branch and the bifurcations being extracted by the eighth embodiment of the present invention.

Next, the eighth embodiment will be described referring to FIGS. 39 and 40.

In the eighth embodiment, the extracting order of the respective bronchial branches is different from the seventh embodiment, and the symmetric property of the right and left in the middle of extraction is not taken into consideration in the seventh embodiment.

Next the extraction order of the respective branches of the bronchi in the eighth embodiment will be explained. In the eighth embodiment, when the bifurcation is reached the extraction toward that direction is stopped once, and the information on the bifurcation is stored. It returns to the previous bifurcation, and extracts the branch in the other direction. It is possible to perform the extraction with a balanced symmetry in the middle of the whole extraction procedure, since each time reaching to the bifurcation it returns to the upper bifurcation by one-tier. In the eighth embodiment, the orders of the extraction for the respective branches are represented with number in FIG. 40. Also, the orders of the extracted bifurcations are represented with circled numbers.

By this eighth embodiment, each bronchial branch can be extracted by every tier with well-balanced symmetry. In the seventh and the eighth embodiments, the extraction results were displayed after completing the extracting process over the whole region. However, it may be displayed at all times 3-dimentionally in the middle of the extraction.

It may be set so that the extraction will end when the extraction-end button is pushed as the operator observes the course of the extraction. By ending the extraction in the middle of the process when there is no need to extract to the peripheral bronchi, the extraction time can be shortened.

The Ninth Embodiment

In the seventh and the eighth embodiments, the extracting process on the branch of each peripheral bronchus is continued until there is no more appropriate bronchi region. However, it may be set so that by setting dimension finishing condition threshold TSfin, when the sub region dimension becomes Sc<TSfin in the middle of the extraction, the extracting process of that branch is finished, and it returns to the bifurcation and performs the extraction on the branch that is not yet extracted. The setting of TSfin can be defined in advance, or the number can be inputted directly by the operator in the dimension-ending condition threshold display region on the interface.

The Tenth Embodiment

Figure 41:
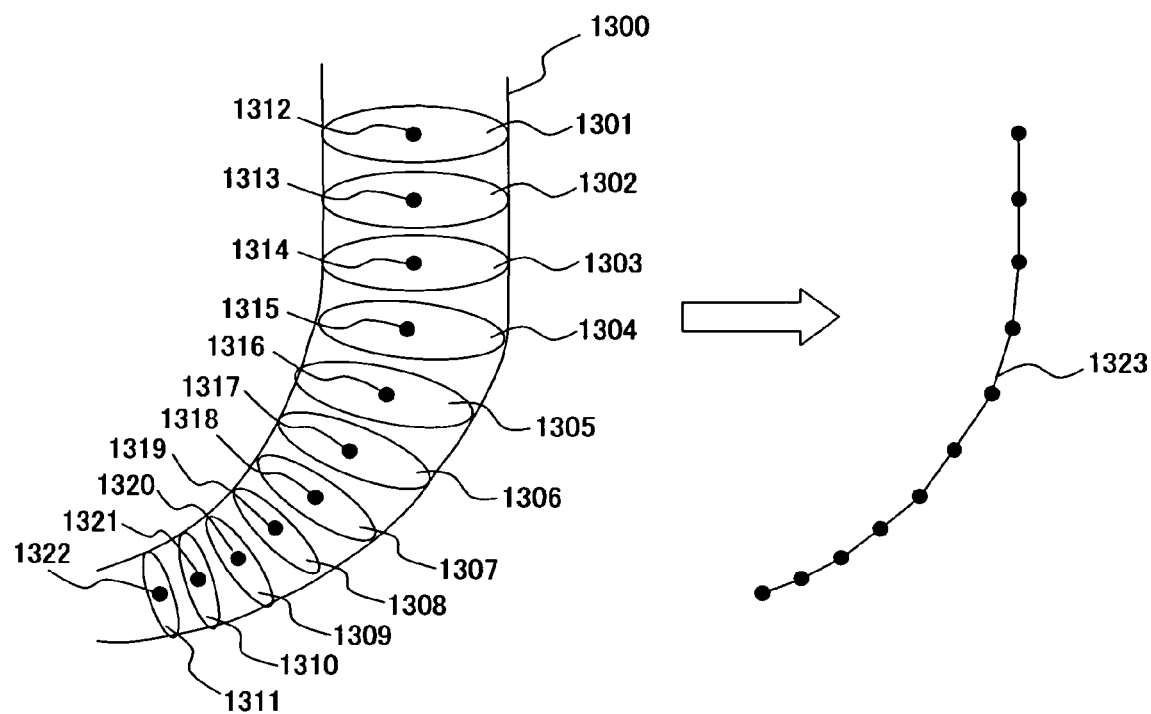
FIG. 41 is an explanatory diagram of the bronchial center-line extraction by the present invention.

It also is possible to extract the centerline of the bronchi from the bronchi region being extracted in the seventh and the eighth embodiments. As illustrated in FIG. 41, in the seventh and eighth embodiments in order to obtain bronchi region 1300, the extraction was executed as obtaining the cross sections 1301~1311 that are orthogonal to the direction of the bronchi. Upon extracting the respective cross-sections, the gravity point coordinates 1312~1322 are obtained as well. Line 1323 that is connecting gravity point coordinates 1312~1322 can be considered as the centerline. When connecting gravity point coordinates 1312~1322, the spacing between adjacent gravity points may be connected. Or the connection may be executed by interpolating such as the spline interpolation.

The Eleventh Embodiment

Figure 42:
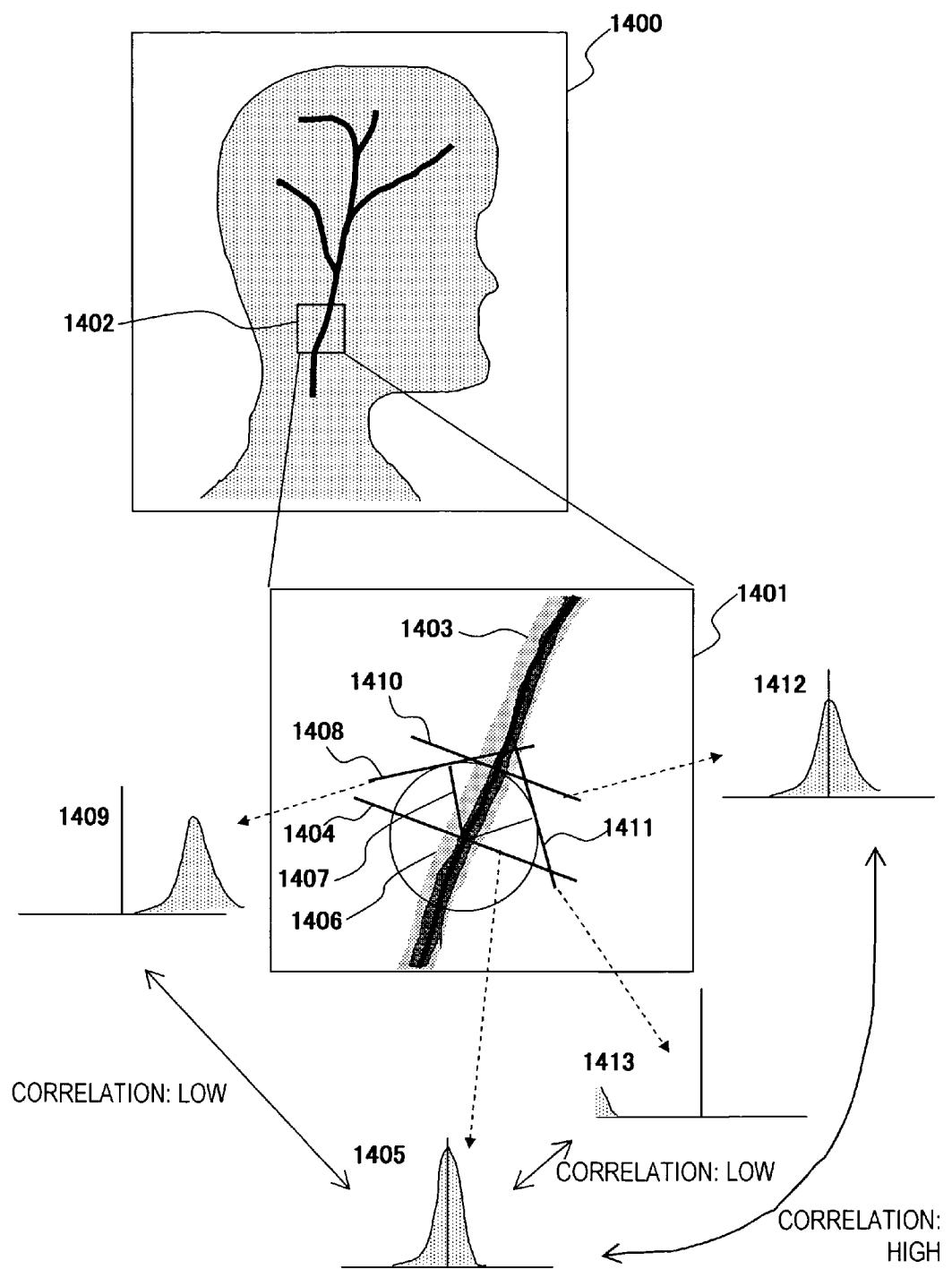
FIG. 42 is an explanatory diagram of the eleventh embodiment of the present invention.

In the seventh through the tenth embodiments, the extraction for the volume data being obtained by the X-ray CT tomography device was described. However, the present invention may have applicability to the extraction of the hollow viscera in 2-dimensional images such as X-ray images. The example of application of the present invention to the 2-dimensional image will be described referring to the FIGS. 42 and 43.

CPU11 extracts a blood vessel from X-ray image 1400 of a head region. As well as the first embodiment, after extracting the early-stage reference region, the next region is extracted using the reference region information. Image 1401 is an enlarged image of region 1402 in image 1400, and the extraction of image 1403 is executed. CPU11 extracts the next region as assuming the blood vessel part on the line segment 1404 as a reference region. The concentration distribution on line segment 1404 is given as illustrated in 1405.

In fact CPU11 obtains the circle with radius 1407 from midpoint 1406 of line segment 1404. CPU11 obtains concentration distribution 1409 of tangent line 1408 on the discretional point on the periphery. CPU11 obtains tangent lines 1410 and 1411 of the respective points on the periphery as well, and also obtains concentration distribution 1412 and 1413 corresponding to the tangent lines.

CPU11 obtains the correlation between concentration distribution 1405 of the reference region and the respective concentration distributions 1409, 1412, and 1413 on the tangent lines, and takes the region that has the highest correlation between concentration distribution 1405 of the reference region as the sub region. In this case, the region that has concentration distribution 1412 on tangent line 1410 is taken as a sub region. By repeating the above-mentioned process of making the selected sub region as a reference region, the extraction of the partial or the whole head region becomes possible.

Figure 43:
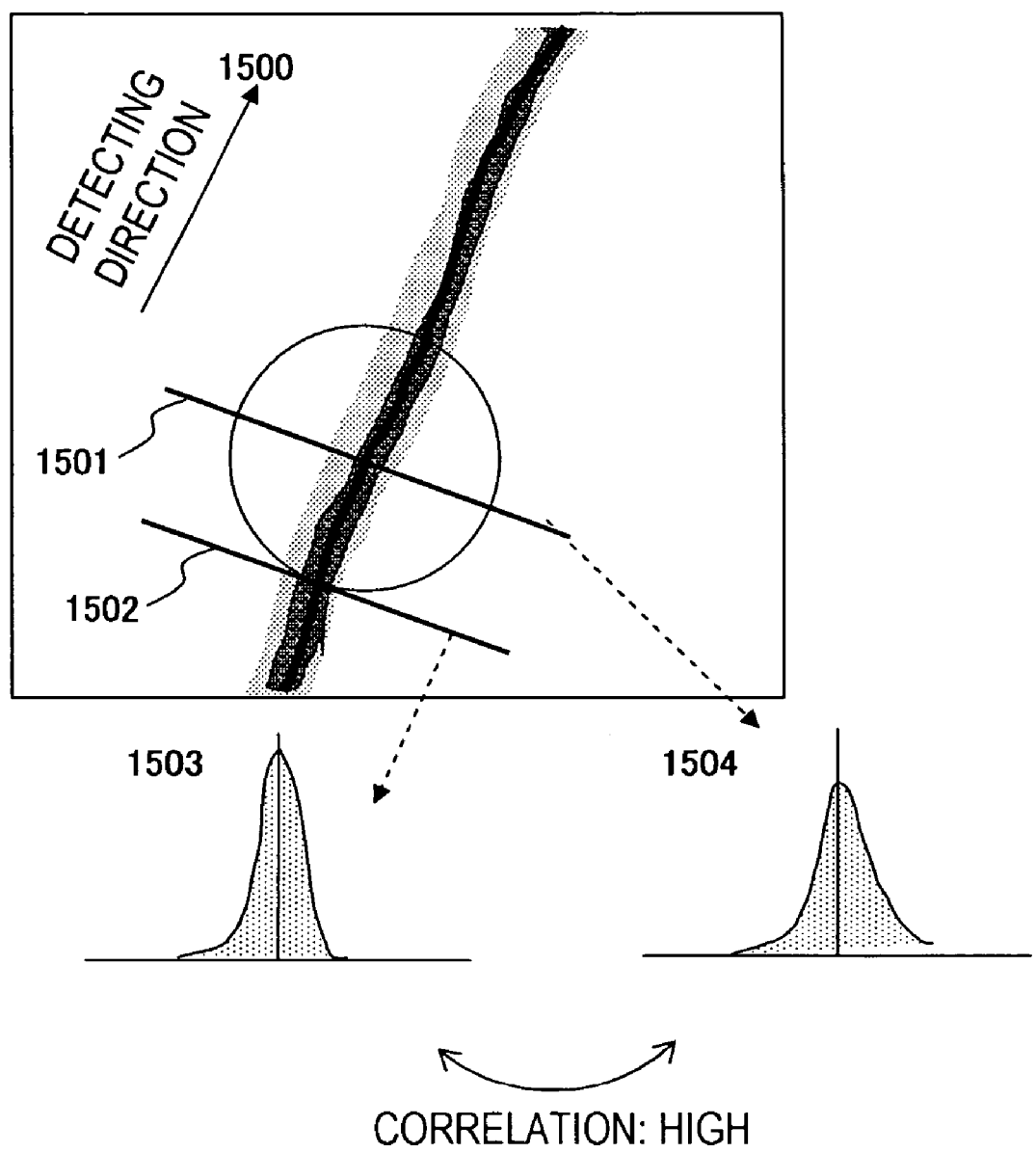
FIG. 43 is an explanatory diagram of the eleventh embodiment of the present invention.

There are some occasions however when the tangent lines on all of the points of the periphery are obtained, that the region already extracted would be extracted again, as illustrated in FIG. 43. In the case of setting 1500 as the direction of extraction and the reference region is on tangent line 1501, the concentration distribution on tangent lines 1501 and 1502 turn out to be the same as 1503 and 1504. Because the correlation of those concentration distributions is high, it is possible that the region that already should be extracted as a sub region would be extracted again. Therefore, the direction for drawing the tangent line on the periphery should be limited, for example, to the region of more than θ° to the right and the left of the line that is connecting the center of the reference region and the center of the region being extracted previously to the reference region.

Though the seventh through the tenth embodiments were described with the bronchi as an example and the eleventh embodiment was described with a blood vessel as an example, the present invention may have applicability to every hollow viscera such as bronchi, blood vessel, and intestinal canal. Also, the modality for taking the images is not limited to a device such as an X-ray CT tomography device, MRI tomography device and ultrasound device. For example, in the case for an image taken by an MRI tomography device wherein the concentration distribution varies moderately over the entire image, the threshold needs to be adjusted and varied accordingly, and the present invention may have applicability to this kind of situation also.

According to the above-mentioned embodiment, it is possible to extract the hollow viscera including the regions where the conventional domain extension method could not extract. Moreover, because the gravity point position of the cross-sections that are orthogonal to the direction of the hollow viscera is obtained in the middle of the extraction, both the hollow viscera and the center lines of the hollow viscera can be extracted in one extraction process without re-obtaining the center lines through the process such as thinning after the extraction, and the direction victors in the respective points on the center line can further be obtained.

Though the plurality of embodiments was described as above, all of the technical contents that achieve the technical ideas being described in the range of the claims are included in the present invention.

INDUSTRIAL AVAILABILITY

The present invention is for diagnosing only the deformed portions on a selective basis, and for presenting the deformation of the diagnosed regions visually through the means such as image display and auditorily through the means such as sounds and voices, which improve the throughput of the diagnosis.

Also, the present invention is for extracting hollow viscera properly through the set thresholds, and for constructing more precise 3-dimensional images from those extracted organ regions.

The invention claimed is:

1. A medical image diagnosis support device, comprising:
   a controller configured through a program of instructions, embodied in a non-transitory form in a computer readable medium, executable by the controller to include the following units:
      an organ region setting unit for setting organ regions in medical images obtained by a medical imaging device;
      a deformation calculating unit for calculating a deformation set of geometric parameters related to deformation from normal shapes of the organ regions set by the organ region setting unit in said medical images;
      a reference storing unit for storing a reference set of geometric parameters related to the normal shapes of the organ regions;
      a lesion detecting unit for detecting existence of at least one lesion in an organ region from amongst the organ regions set by the organ region setting unit based on comparing the reference set of geometric parameters stored by the reference storing unit with the deformation set of geometric parameters calculated by the deformation calculating unit; and
      an informing unit for providing at least visual information informing the existence of the lesion in the organ region detected by the lesion detecting unit,
      wherein the visual information includes a chart showing changes of geometric parameters as between the deformation set of geometric parameters of a deformed organ and the reference set of geometric parameters.

2. The medical image diagnosis support device according to claim 1,
wherein the deformation calculation unit comprises:
a bifurcation detecting unit for detecting bifurcation into branches of an organ region from amongst said organ regions;
a unit for creating a plurality of cross-sections of the organ region diverged by the bifurcation detected by the bifurcation detecting unit; and
a distance calculating unit for calculating distances between or to said branches in each of the plurality of cross-sections, and
wherein the lesion detecting unit detects the existence of the lesion in the organ region based on including said distances in said deformation set of geometric parameters.

3. The medical image diagnosis support device according to claim 1, wherein the reference storing unit stores a plurality of templates related to different sets of said reference geometric parameters.

4. The medical image diagnosis support device according to claim 1, wherein the deformation calculating unit includes:
a cross-sectional image calculating unit for calculating cross-sectional images that are orthogonal to axial direction of an organ region from amongst said organ regions; and
an extracting unit for extracting a lumen and an exterior of the organ region from the cross-sectional images calculated by the cross-sectional image calculating unit and calculating a deformation set of parameters related to deformation of the lumen and the exterior of the organ region extracted by the extracting unit.

5. The medical image diagnosis support device according to claim 1, wherein the deformation calculating unit includes:
an extracting unit for extracting hollow viscera from an organ region amongst said organ regions;
a notable region setting unit for setting a notable region of the hollow viscera extracted by the extracting unit; and
an unit for creating cross-sectional images of the hollow viscera extracted by the extracting unit based on the notable region set by the notable region setting unit, and
wherein the lesion detecting unit detects the existence of the lesion of the organ region based on deformation of the cross-sectional images of the hollow viscera.

6. The medical image diagnosis support device according to claim 1, wherein the informing unit informs the existence of the lesion visually by displaying the lesion through colors or movement in displayed images.

7. The medical image diagnosis support device according to claim 6, wherein the informing unit displays visual presentation by displaying cross-sectional images of the organ regions, and by highlighting lesion candidate portions detected by the lesion detecting unit, on the cross-sectional images.

8. The medical image diagnosis support device according to claim 1, wherein the informing unit informs the existence of the lesion auditorily by outputting it through voices and sounds, or a variance of the voices and sounds.

9. The medical image diagnosis support device according to claim 1, wherein said controller configured through the program of instructions further includes:
a cross-section extracting unit for extracting cross sections from a feature quantity of hollow viscera on the medical images obtained by the medical imaging device;
a physical quantity calculating unit for calculating a physical quantity including radius, degree of circularity, and gravity point of the hollow viscera on the hollow viscera cross-sections extracted by the extracting unit;
an ROI calculating unit for calculating a region of interest based on the physical quantity calculated by the physical quantity calculating unit;
a 3-dimensional image creating unit for creating 3-dimensional images of the hollow viscera from the medical images including the cross sections of the hollow viscera extracted by the cross section extracting unit within the region of interest calculated by the ROI calculating unit; and
an image displaying unit for displaying the 3-dimensional images created by the 3-dimensional image creating unit.

10. The medical image diagnosis support device according to claim 9, wherein said controller configured through the program of instructions further includes a center-line calculating unit for calculating a center line of the hollow viscera based on the gravity point of the hollow viscera cross sections calculated by the physical quantity calculating unit, wherein the image display unit displays the center line calculated by the center-line calculating unit together with the 3-dimensional images created by the 3-dimensional image creating unit.

11. A medical image diagnosis support method comprises:
an organ region setting step of setting organ regions in medical images obtained by a medical imaging device;
a deformation calculating step of calculating a deformation set of geometric parameters related to deformation from normal shapes of the organ regions set in the organ region setting step;
a reference storing step of storing a reference set of geometric parameters related to normal shapes of the organ regions;
a lesion detecting step of comparing the reference set of geometric parameters stored in the reference storing step with the deformation set of geometric parameters calculated in the deformation calculating step, and detecting existence of lesion in an organ region from amongst the organ regions set in the organ region setting step, from a result of the comparison; and
an informing step of providing at least visual information informing the existence of the lesion, wherein the visual information includes a chart showing changes of geometric parameters as between the deformation set of geometric parameters of a deformed organ and the reference set of geometric parameters.

12. The medical image diagnosis support method according to claim 11, further comprising:
detecting bifurcation into branches of an organ region from amongst said organ regions;
creating a plurality of cross-section images of the bifurcated organ region; and
calculating distances between or to said branches in each of the plurality of cross-sectional images, and
wherein the lesion detecting step detects the existence of the lesion of the organ region based on including said distances in the deformation set of geometric parameters.

13. The medical image diagnosis support method according to claim 11, further comprising:
storing a plurality of templates related to different sets of said reference geometric parameters.

14. The medical image diagnosis support method according to claim 11, further comprising:
- a cross-sectional image calculating step for calculating cross-sectional images that are orthogonal to an axial direction of an organ region from amongst said organ regions; and
- an extracting step for extracting a lumen and an exterior of the organ region from the cross-sectional images calculated in the cross-sectional image calculating step, and calculating a deformation of the lumen and the exterior of the organ region.

15. The medical image diagnosis support method according to claim 11, wherein further comprising:
- an extracting step for extracting hollow viscera out of the organ regions set in the organ region setting step;
- a notable region setting step for setting a notable region of the hollow viscera extracted in the extracting step; and
- a step for creating cross-sectional images of the hollow viscera extracted in the extracting step based on the notable region set in the notable region setting step, and
- wherein the lesion detecting step detects the existence of the lesion of the organ region based on the deformation of the cross-sectional images of the hollow viscera.

16. The medical image diagnosis support method according to claim 11, wherein the informing step informs the existence of the lesion visually through displaying the lesion by at least one of color tinting and/or movement on a displayed image.

17. The medical image diagnosis support method according to claim 16, wherein the informing step includes displaying cross-sectional images of the organ regions set by the organ region setting step, and highlighting a lesion candidate portion on the cross-sectional images.

18. The medical image diagnosis support method according to claim 11, wherein the informing step informs the existence of the lesion auditorily through outputting by at least one of voices, and/or sounds and a variance of voices and/or sounds.

19. The medical image diagnosis support method according to claim 11 further comprising:
- a cross-sectional image extracting step for extracting cross sections from a feature quantity of hollow viscera in cross-sectional images obtained by the medical imaging device;
- a physical quantity calculating step for calculating a physical quantity including radius, degree of circularity and gravity point of the hollow viscera on the cross-sectional images;
- an ROI calculating step for calculating a region of interest based on the physical quantity calculated in the physical quantity calculating step;
- a 3-dimensional creating step for creating 3-dimensional images of the hollow viscera from the cross-sectional images including the cross-section of the hollow viscera within the region of interest; and
- an image displaying step for displaying the 3-dimensional images.

20. The medical image diagnosis support method according to claim 19, further comprising:
- a center line calculating step for calculating a center line of the hollow viscera based on the gravity point of the cross section of the hollow viscera calculated in the physical quantity calculating step,
- wherein the image display step displays the center line calculated in the center line calculating step together with the 3-dimensional images created in the 3-dimensional image creating step.

\* \* \* \* \*